United States Patent
Narusawa et al.

(10) Patent No.: US 10,201,287 B2
(45) Date of Patent: Feb. 12, 2019

(54) BIOLOGICAL INFORMATION DETECTING DEVICE AND ELECTRONIC APPARATUS

(71) Applicant: Seiko Epson Corporation, Tokyo (JP)

(72) Inventors: Atsushi Narusawa, Chino (JP); Yu Gu, Fuchu (JP)

(73) Assignee: Seiko Epson Corporation, Tokyo (JP)

( * ) Notice: Subject to any disclaimer, the term of this patent is extended or adjusted under 35 U.S.C. 154(b) by 233 days.

(21) Appl. No.: 15/120,092

(22) PCT Filed: Mar. 23, 2015

(86) PCT No.: PCT/JP2015/001639
§ 371 (c)(1),
(2) Date: Aug. 18, 2016

(87) PCT Pub. No.: WO2015/146139
PCT Pub. Date: Oct. 1, 2015

(65) Prior Publication Data
US 2017/0055861 A1    Mar. 2, 2017

(30) Foreign Application Priority Data
Mar. 27, 2014  (JP) ................ 2014-065981

(51) Int. Cl.
*A61B 5/00* (2006.01)
*A61B 5/024* (2006.01)

(52) U.S. Cl.
CPC ...... *A61B 5/02438* (2013.01); *A61B 5/02416* (2013.01); *A61B 5/02427* (2013.01);
(Continued)

(58) Field of Classification Search
CPC ............ A61B 5/02438; A61B 5/02416; A61B 5/02427; A61B 5/681; A61B 5/6843;
(Continued)

(56) References Cited

U.S. PATENT DOCUMENTS 6,198,951 B1    3/2001  Kosuda et al.
2004/0193063 A1    9/2004  Kimura et al.
(Continued)

FOREIGN PATENT DOCUMENTS

EP    1444948 A1    8/2004
JP    55-120858 A    9/1980
(Continued)

OTHER PUBLICATIONS

Extended European Search Report received in EP Application No. 15769454 dated Nov. 2, 2017.
(Continued)

*Primary Examiner* — Paula J Stice
(74) *Attorney, Agent, or Firm* — ALG Intellectual Property, LLC

(57) ABSTRACT

A biological information detecting device includes: a first light receiving portion which receives light from a subject; a second light receiving portion which receives light from the subject; and a light-transmissive member which is provided at a position further on the subject side than the first light receiving portion and the second light receiving portion, through which light from the subject is transmitted. In a direction from the biological information detecting device to the subject, when a height of the light-transmissive member at a position or in a region corresponding to the first light receiving portion is set to h1 and a height of the light-transmissive member at a position or in a region corresponding to the second light receiving portion is set to h2, h1>h2 is satisfied.

20 Claims, 21 Drawing Sheets

(52) U.S. Cl.
CPC ............ *A61B 5/681* (2013.01); *A61B 5/6843* (2013.01); *A61B 5/721* (2013.01); *A61B 5/7214* (2013.01); *A61B 2560/0412* (2013.01); *A61B 2562/0238* (2013.01); *A61B 2562/0242* (2013.01); *A61B 2562/146* (2013.01)

(58) Field of Classification Search
CPC ..... A61B 5/721; A61B 5/7214; A61B 5/7203; A61B 2560/0412; A61B 2562/0268; A61B 2562/0242; A61B 2562/146
See application file for complete search history.

(56) References Cited

U.S. PATENT DOCUMENTS

| | | | |
|---|---|---|---|
| 2005/0075553 | A1 | 4/2005 | Sakai et al. |
| 2013/0267854 | A1 | 10/2013 | Johnson et al. |
| 2016/0287181 | A1* | 10/2016 | Han .................... A61B 5/7214 |

FOREIGN PATENT DOCUMENTS

| | | |
|---|---|---|
| JP | 2004-261366 A | 9/2004 |
| JP | 2005-246089 A | 9/2005 |
| JP | 2009-39568 A | 2/2009 |
| WO | WO-1999-12469 A | 3/1999 |

OTHER PUBLICATIONS

International Search Report, Internation Application No. PCT/JP2015/001639, dated Jun. 16, 2015.

* cited by examiner

BIOLOGICAL INFORMATION DETECTING DEVICE AND ELECTRONIC APPARATUS

CROSS-REFERENCE TO RELATED APPLICATIONS

This application is the U.S. National Phase under 35 U.S.C. § 371 of International Application No. PCT/JP2015/001639 filed on Mar. 23, 2015, which in turn claims the benefit of Japanese Application No. 2014-065981 filed on Mar. 27, 2014, the disclosures of which are expressly incorporated by reference herein.

TECHNICAL FIELD

The present invention relates to a biological information detecting device, an electronic apparatus, or the like.

BACKGROUND ART

A pulse wave represents a change in the volume of blood, and therefore, a photoelectric pulse wave sensor can measure the pulse wave by capturing the change in the volume of blood in a site to be measured. However, the volume of blood in a portion to be measured also changes due to movement (hereinafter, referred to as body motion) of a human body in addition to pulsation (that is, pulse wave) of the heart. For this reason, at the time of measuring a pulse wave using the photoelectric pulse wave sensor, in some cases, a noise due to body motion is included in wave motion in the process of propagation of the pulse wave from the heart to a site to be measured. That is, blood is a fluid and blood vessels are elastic, and therefore, in some cases, the flow of blood, which is caused by body motion, causes a change in the volume of blood and is measured as pseudo pulsation.

A pulse wave measuring device which performs calculation processing in order to remove a noise component due to such body motion has been developed. For example, PTL 1 discloses a technique of emitting light having different wavelengths, measuring reflected light thereof at the same time, and extracting a pulsation component from the measured value. This technique uses the fact that there are different extinction characteristics between oxygenated hemoglobin which is dominant in arterial blood and reduced hemoglobin which is dominant in venous blood.

CITATION LIST

Patent Literature

PTL 1: JP-A-55-120858

SUMMARY OF INVENTION

Technical Problem

However, the irradiation light having different wavelengths which is used in a sensor that measures a pulse wave by detecting reflected light also has different penetration depths of light into a living body. For this reason, in the technique disclosed in PTL 1, the difference in absorbance which is caused by a plurality of sensors also includes an influence caused by the differences in the penetration depths of light having different wavelengths, and therefore, it is difficult to reduce the noise caused by body motion.

Solution to Problem

An advantage of some aspects of the invention is that it is possible to provide a biological information detecting device which detects signals having different characteristics while having correlations in each light receiving portion of a plurality of light receiving portions to some extent, by having an appropriate structure, an electronic apparatus, etc.

Another advantage of some aspects of the invention is that it is possible to provide a biological information detecting device which reduces a body motion noise based on the signals which have different characteristics and are detected in each light receiving portion of the plurality of light receiving portions, an electronic apparatus, etc.

An aspect of the invention relates to a biological information detecting device including: a first light receiving portion which receives light from a subject; a second light receiving portion which receives light from the subject; and a light-transmissive member which is provided at a position further on the subject side than the first light receiving portion and the second light receiving portion, through which light from the subject is transmitted, and which applies a pressing force by coming into contact with the subject at the time of measuring biological information of the subject. In a direction from the biological information detecting device to the subject, when a height of the light-transmissive member at a position or in a region corresponding to the first light receiving portion is set to h1 and a height of the light-transmissive member at a position or in a region corresponding to the second light receiving portion is set to h2, h1>h2 is satisfied.

According to the aspect of the invention, the heights of the light-transmissive member at positions or regions respectively corresponding to the first light receiving portion and the second light receiving portion may be different from each other. Accordingly, it is possible to provide a difference in the pressing force, for example. Therefore, it is possible to make the characteristics of a first detection signal from the first light receiving portion and the characteristics of a second detection signal from the second light receiving portion be different from each other. Thus, it is possible to detect biological information based on the first and second detection signals which have different characteristics from each other.

In the aspect of the invention, the height h1 may be a height of the light-transmissive member at a representative position of the first light receiving portion, and the height h2 may be a height of the light-transmissive member at a representative position of the second light receiving portion.

With this configuration, it is possible to set heights of the light-transmissive members corresponding to the light receiving portions based on the representative positions of the light receiving portions.

In the aspect of the invention, the biological information detecting device may further include at least one light emitting portion emitting light to the subject. When a region including the first light receiving portion and the light emitting portion in a plan view seen from the subject side is set to a first region and a region including the second light receiving portion and the light emitting portion in a plan view seen from the subject side is set to a second region, the height h1 may be an average height of the light-transmissive member in the first region and the height h2 may be an average height of the light-transmissive member in the second region.

With this configuration, it is possible to set the heights of the light-transmissive members corresponding to the light receiving portions using the average heights in the first and second regions.

In the aspect of the invention, at the time of measuring the biological information of the subject, when a pressing force of the light-transmissive member at a position or in a region corresponding to the first light receiving portion is set to P1 and a pressing force of the light-transmissive member at a position or in a region corresponding to the second light receiving portion is set to P2, P1>P2 may be satisfied.

With this configuration, it is possible to provide a difference in the pressing force, and therefore, it is possible to make the characteristics of a first detection signal from the first light receiving portion and the characteristics of a second detection signal from the second light receiving portion be different from each other, or the like.

In the aspect of the invention, the biological information detecting device may further include a processing portion which calculates the biological information of the subject based on a first detection signal detected by the first light receiving portion.

With this configuration, it is possible to calculate the biological information based on the first detection signal.

In the aspect of the invention, the biological information detecting device may further include at least one light emitting portion which emits light to the subject, and the first light receiving portion may be disposed between the light emitting portion and the second light receiving portion.

With this configuration, it is possible to appropriately dispose the light emitting portion and the plurality of light receiving portions, or the like.

In the aspect of the invention, when a distance between the light emitting portion and the first light receiving portion is set to L1 and a distance between the light emitting portion and the second light receiving portion is set to L2, L2>2×L1 may be satisfied.

With this configuration, it is possible to appropriately set the distance between the light emitting portion and each of the light receiving portions, or the like.

In the aspect of the invention, the biological information detecting device may further include at least one light emitting portion which emits light to the subject, and when a distance between the light emitting portion and the first light receiving portion is set to L1 and a distance between the light emitting portion and the second light receiving portion is be set to L2. L2>L1 may be satisfied.

With this configuration, it is possible to appropriately set the distance between the light emitting portion and each of the light receiving portions, or the like.

In the aspect of the invention, the distance L1 between the light emitting portion and the first light receiving portion may satisfy 1 mm<=L1<=3 mm, and the distance L2 between the light emitting portion and the second light receiving portion may satisfy 2 mm<=L2.

With this configuration, it is possible to appropriately set the distance between the light emitting portion and each of the light receiving portions, or the like.

In the aspect of the invention, the biological information detecting device may further include at least one light emitting portion emitting light to the subject, and the light emitting portion may be disposed between the first light receiving portion and the second light receiving portion.

With this configuration, it is possible to appropriately dispose the light emitting portion and the plurality of light receiving portions, or the like.

In the aspect of the invention, the biological information detecting device may further include a contact portion which is provided around the light-transmissive member and comes into contact with the subject at the time of measuring the biological information of the subject, and when a height at a position or in a region corresponding to the contact portion is set to h3, h1>h3>h2 may be satisfied.

With this configuration, it is possible to appropriately set the relationship between the heights of the light-transmissive members corresponding to the light receiving portions and the height of the contact portion, or the like.

In the aspect of the invention, the light-transmissive member may have a curved surface-like convex portion.

With this configuration, it is possible to appropriately apply pressing force using the curved surface-like convex portion, or the like.

Another aspect of the invention relates to an electronic apparatus including the biological information detecting device described above.

BRIEF DESCRIPTION OF DRAWINGS

The invention will be described with reference to the accompanying drawings, wherein like numbers reference like elements.

DESCRIPTION OF EMBODIMENTS

Figure 1A:
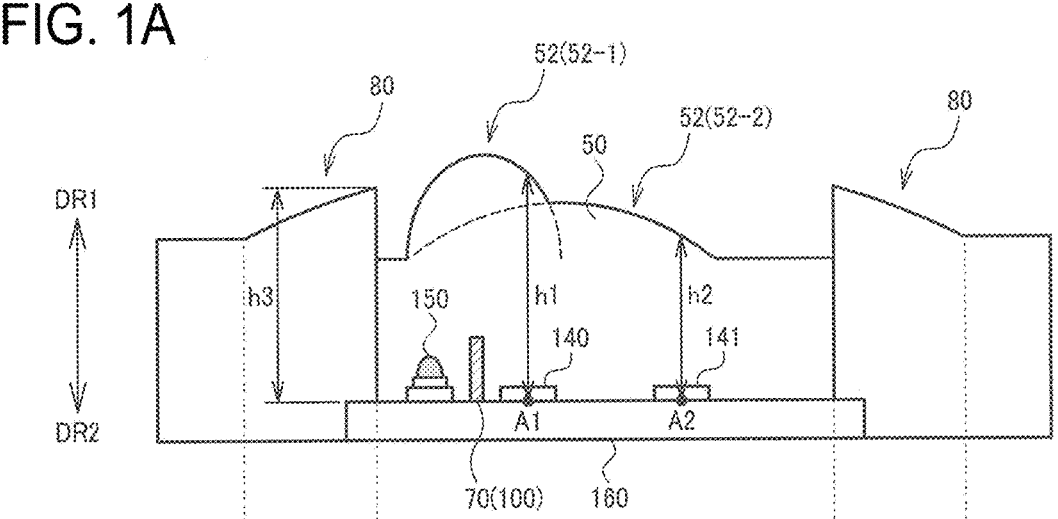
FIG. 1 shows a cross-sectional view and a plan view showing a disposition example of first and second light receiving portions in the present embodiment.

Hereinafter, the present embodiment will be described. The present embodiment described below does not unjustly limit the content of the invention described in the appended claims. In addition, all of the configurations described in the present embodiment are not necessarily essential configuration requirements of the invention.

1. Technique of Present Embodiment

First, a technique of the present embodiment will be described. As described above, when detecting biological information such as pulse wave information using a photoelectric sensor, a noise due to body motion causes a problem. For this reason, when accurately detecting biological information, it is necessary to reduce the body motion noise using some technique.

When reducing the body motion noise, a component corresponding to the body motion noise is reduced (removed in a narrow sense) while maintaining a component corresponding to a pulse signal as much as possible among detection signals of the photoelectric sensor. That is, in the body motion noise reduction processing, it is necessary to know which signal component corresponds to the body motion noise.

On the contrary, a technique of reducing body motion noise using a motion sensor has been known. The motion sensor is a sensor for detecting movement of a user (wearer of a biological information detecting device), and therefore, it is possible to obtain a signal corresponding to body motion, that is, a signal corresponding to a body motion noise using the motion sensor. Here, an acceleration sensor, a gyro sensor, an atmospheric pressure sensor, or the like can be considered as the motion sensor.

The technique of reducing body motion noise using the above-described motion sensor may also be used together in the present embodiment. However, the present applicant suggests another technique of reducing body motion noise. Specifically, a signal in which a large number of body motion noises are included is acquired using a second light receiving portion which is different from a first light receiving portion that detects a pulse signal.

As described above, the body motion noises are included in detection signals in the photoelectric sensor. It is possible to mainly acquire the detection signals including the body motion noises using the second light receiving portion in which the sensitivity of a pulse signal is purposely set to be low and the sensitivity of a body motion noise is purposely set to be high, using such a point.

If it is possible to detect the signal corresponding to a body motion noise in the second light receiving portion, it becomes possible to reduce the body motion noise by removing (reducing) the component corresponding to a detection signal in the second light receiving portion from a detection signal in the first light receiving portion. At this time, the sensitivity of a pulse signal is low in the second light receiving portion, and therefore, the pulse component included in the detection signal of the first light receiving portion will not be excessively reduced.

However, in order to enable such processing, it is necessary that the characteristics (for example, frequency characteristics) of body motion noises included in the detection signals in the first light receiving portion and the second light receiving portion be identical to each other (or be sufficiently close to each other). That is, the detection signals of the two light receiving portions need to be closely correlated to each other while providing a difference in the detection characteristics such that the first light receiving portion mainly detects a pulse signal and the second light receiving portion mainly detects a body motion noise.

In the technique disclosed in PTL 1, frequency bands of light beams detected by each of a plurality of light receiving portions are very different from each other. For this reason, even if it is possible to make the characteristics of the detection signals from each of the light receiving portions be different from each other, it is somewhat difficult to provide correlations therebetween. This is because if the wavelengths of light beams are different from each other, the permeation depths into a living body are also different from each other, and therefore, the structure of blood vessels, bones, and the like, which are detection targets, become different from each other in the first place.

For this reason, in the present embodiment, an identical wavelength band of light is used in the plurality of light receiving portions. The light in the identical wavelength band does not mean that a wavelength having maximum intensity is completely identical, and indicates that the wavelength having the maximum intensity falls within a predetermined range (for example, range of an identical color). The light emitted from a light emitting portion 150 is light in a wavelength band included in a range of, for example, 470 nm to 610 nm. More specifically, the light emitted from the light emitting portion 150 is light in a wavelength band included in a range of 520 nm to 570 nm. The light in this wavelength band is more easily reflected from hemoglobin in blood vessels compared to light in other wavelength bands.

In the present specification below, as described above, a specific configuration of a biological information detecting device that satisfies the requirements that the characteristics of detection signals are different in each of the light receiving portions while providing correlations therebetween to some degree, will be described. As will be described later using FIGS. 8 to 12, it is known that sensitivity with respect to a pulse signal or sensitivity with respect to a body motion noise changes depending on the pressing force applied to a subject, or the distance between the light emitting portion and the light receiving portions. Moreover, it is possible to adjust the pressing force applied to the subject depending on the height of a member (light-transmissive member to be described later in a narrow sense) coming into contact with the subject at a position or in a region corresponding to the light receiving portions.

That is, hereinafter, a specific configuration of a biological information detecting device which includes a method of setting the height of the light-transmissive member at a position or in a region corresponding to a light receiving portion and the distance between the light emitting portion and light receiving portions, and has a height or a distance which is appropriately set using the technique, will be described.

Figure 1B:
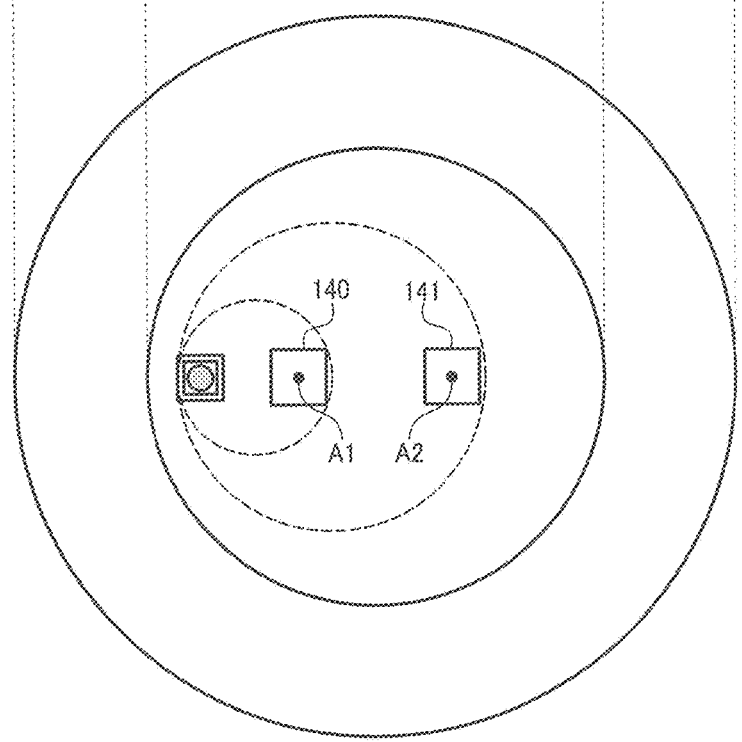

For example, the biological information detecting device according to the present embodiment includes a first light receiving portion 140 which receives light from a subject; a second light receiving portion 141 which receives light from the subject; and a light-transmissive member 50 which is provided at a position further on the subject side than the first light receiving portion 140 and the second light receiving portion 141, through which light from the subject is transmitted, and which applies a pressing force by coming into contact with the subject at the time of measuring the biological information of the subject. As shown in FIGS. 1A and 1B, in a direction (DR1) from the biological information detecting device to the subject, when the height of the light-transmissive member 50 at a position or in a region corresponding to the first light receiving portion is set to h1 and the height of the light-transmissive member 50 at a position or in a region corresponding to the second light receiving portion is set to h2, h1>h2 is satisfied.

A configuration (in particular, the height or the shape of the light-transmissive member 50) of the biological information detecting device according to the present embodiment is schematically shown in FIGS. 1A and 1B for simplification, and the dimensions or the proportions which are shown in the drawings are different from those in reality. In addition, this point is also applied to the drawings after FIG. 2A.

At this time, as will be described later using FIG. 6, the biological information detecting device may include a processing portion 200 that calculates the biological information of a subject based on a first detection signal detected by the first light receiving portion 140. In this manner, it is possible to calculate biological information such as a pulse using the first detection signal from the first light receiving portion 140.

Figure 2A:
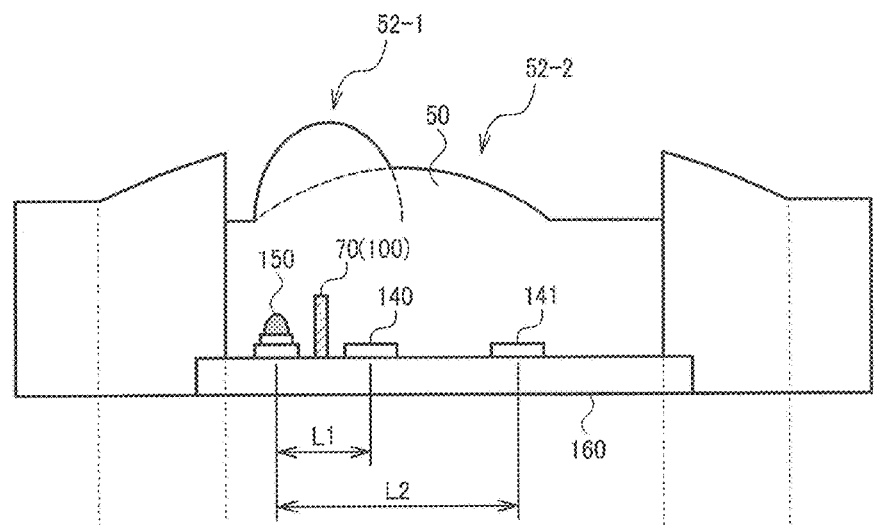
FIG. 2 shows views illustrating the distance between the first and second light receiving portions and a light emitting portion.
Figure 2B:
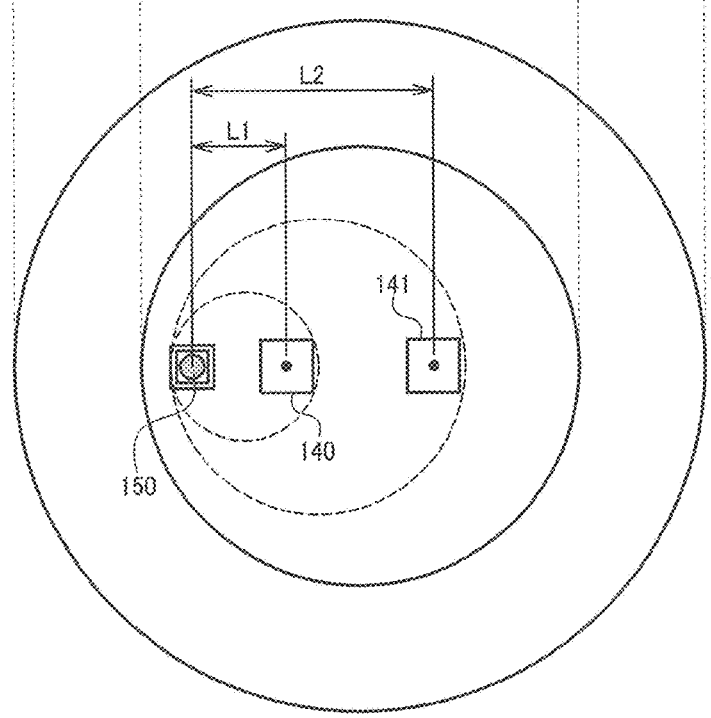

In addition, the biological information detecting device according to the present embodiment includes the first light receiving portion 140 which receives light from a subject; the second light receiving portion 141 which receives light from the subject; the processing portion 200; and at least one light emitting portion 150 which emits light with respect to the subject. When the distance between the light emitting portion 150 and the first light receiving portion 140 is set to L1 and the distance between the light emitting portion 150 and the second light receiving portion 141 is set to L2, L1<L2 is satisfied as shown in FIGS. 2A and 2B. The processing portion 200 performs body motion noise reduction processing that reduces a body motion noise in the first detection signal detected by the first light receiving portion 140 based on a second detection signal detected by the second light receiving portion 141, and calculates biological information based on the first detection signal after the body motion noise reduction processing.

In this manner, it is possible to mainly detect a pulse signal in the first light receiving portion 140 and a body motion noise in the second light receiving portion 141 as described above by providing a difference in at least one of the height of the light-transmissive member at a position or in a region corresponding to each light receiving portion, and the distance between each light receiving portion and the light emitting portion. For this reason, it is possible to perform body motion noise reduction processing using the second detection signal of the second light receiving portion 141 with respect to the first detection signal of the first light receiving portion 140, to accurately obtain biological information from the first detection signal after the body motion noise reduction processing, or the like.

Figure 3A:
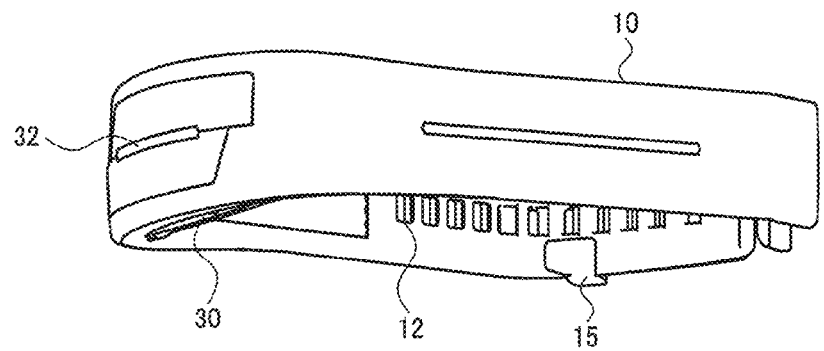
FIG. 3A is an external view of a biological information detecting device of the present embodiment.
Figure 3B:
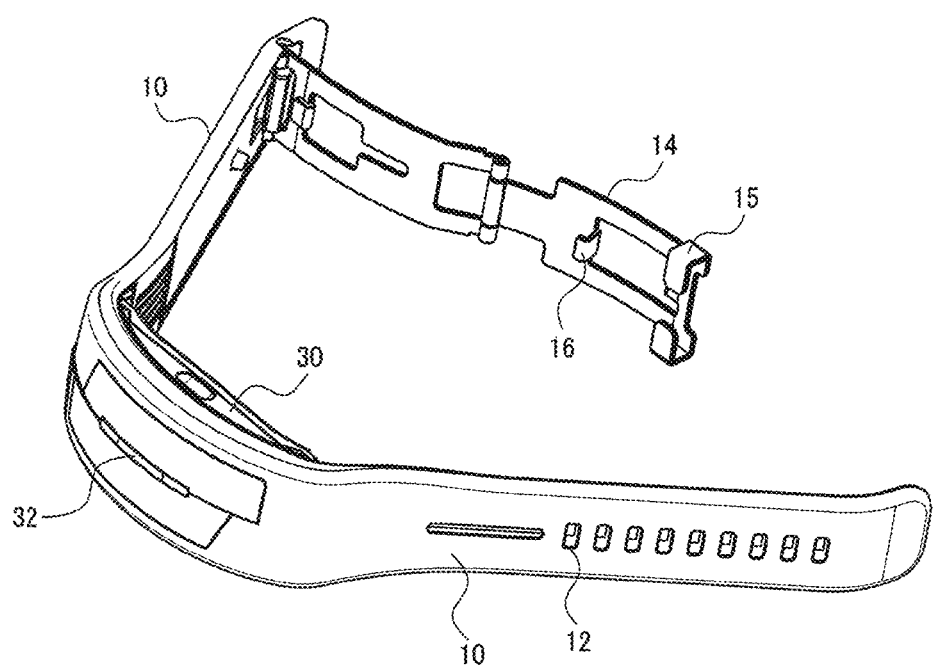
FIG. 3B is an external view of a biological information detecting device of the present embodiment.
Figure 4:
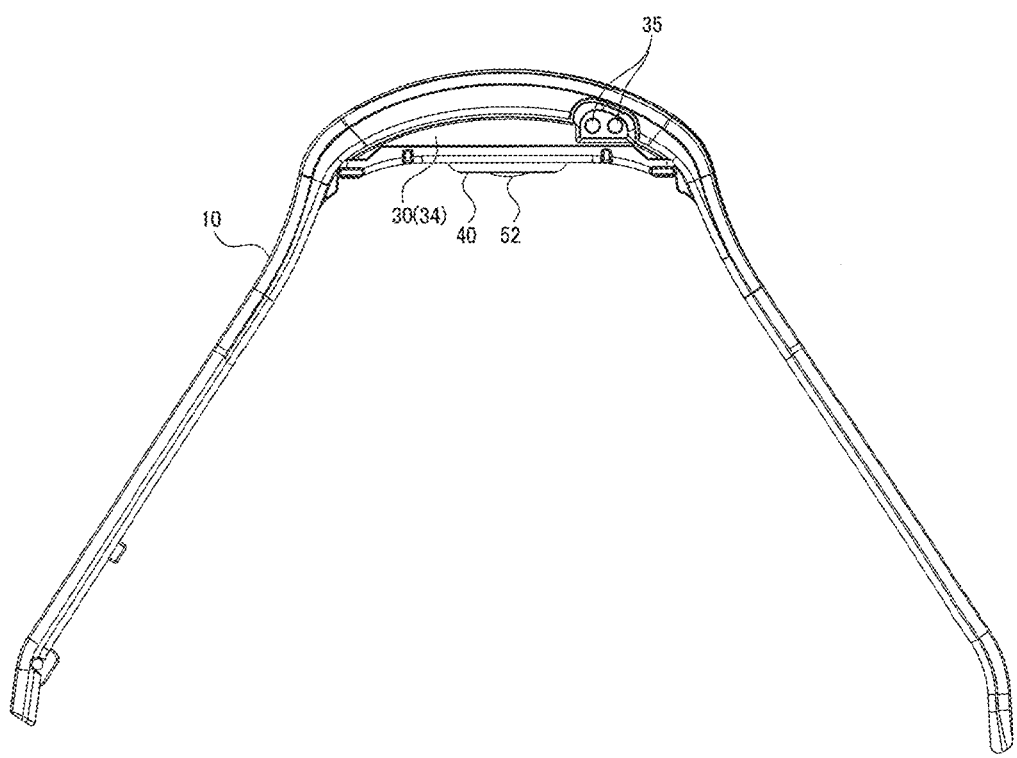
FIG. 4 is an external view of the biological information detecting device according to the present embodiment.

2. Configuration Example of Biological Information Detecting Device or the Like 2.1 Overall Configuration Example of Biological Information Detecting Device External views of a biological information detecting device (biological information measuring device) of the present embodiment are shown in FIGS. 3A to 4. FIG. 3A is a view in which the biological information detecting device is viewed from a frontward direction, FIG. 3B is a view in which the biological information detecting device is viewed from above, and FIG. 4 is a view seen from a side surface direction.

As shown in FIGS. 3A to 4, the biological information detecting device of the present embodiment has a band portion 10, a case portion 30, and a sensor portion 40. The case portion 30 is attached to the band portion 10. The sensor portion 40 is provided on the case portion 30. In addition, the biological information detecting device has the processing portion 200 to be described later as shown in FIG. 6. The processing portion 200 is provided in the case portion 30 and detects biological information based on a detection signal from the sensor portion 40. The biological information detecting device of the present embodiment is not limited to the configurations shown in FIGS. 3A to 4, and it is possible to perform various modifications, for example, omitting a part of constituents, replacing the constituents with other constituents, and adding other constituents.

The band portion 10 is used to install the biological information detecting device by winding the biological information detecting device around the wrist of a user. The band portion 10 has a band hole 12 and a buckle portion 14. The buckle portion 14 has a band insertion portion 15 and a protrusion portion 16. A user inserts an end of the band portion 10 into the band insertion portion 15 of the buckle portion 14 and inserts the protrusion portion 16 of the buckle portion 14 into the band hole 12 of the band portion 10 to place the biological information detecting device on the wrist. In this case, the magnitude of the pressing force (pressing force with respect to a surface of the wrist) of the sensor portion 40 to be described later is adjusted depending on which band hole 12 is inserted with the protrusion portion 16.

The case portion 30 corresponds to a main body portion of the biological information detecting device. Various components of the biological information detecting device such as the sensor portion 40 and the processing portion 200 are provided in the case portion 30. That is, the case portion 30 is a housing for storing these components. The case portion 30 has, for example, a top case 34 and a bottom case 36. The case portion 30 may not be in a mode in which the case portion 30 is separated into the top case 34 and the bottom case 36.

The case portion 30 is provided with a light emitting window portion 32. The light emitting window portion 32 is formed of a light-transmissive member. The case portion 30 is provided with a light emitting portion (LED: light emitting portion for notification which is different from the light emitting portion 150 of a photodetection unit) which is mounted on a flexible substrate, and light from the light emitting portion is emitted to the outside of the case portion 30 through the light emitting window portion 32.

As shown in FIG. 4, the case portion 30 is provided with a terminal portion 35. When the biological information detecting device is mounted on a cradle which is not shown, a terminal portion of the cradle and the terminal portion 35 of the case portion 30 are electrically connected to each other. Accordingly, it is possible to charge a secondary battery provided in the case portion 30.

The sensor portion 40 detects biological information such as the pulse wave of a subject. For example, the sensor portion 40 has the first light receiving portion 140, the second light receiving portion 141, and the light emitting portion 150, as illustrated in FIG. 1A or the like. In addition, the sensor portion 40 has a convex portion 52 which is formed of a light-transmissive member 50 and is coming into contact with the surface of the skin of the subject so as to apply a pressing force. In a state in which the convex portion 52 applies a pressing force on the surface of the skin in this manner, the light emitting portion 150 emits light which is then reflected by a subject (blood vessel) and is received by the first light receiving portion 140 and the second light receiving portion 141. The result of light reception is output to the processing portion 200 as a first detection signal and a second detection signal. Then, the processing portion 200 performs noise reduction processing on the first detection signal based on the second detection signal from the sensor portion 40 and detects biological information such a pulse wave based on the first detection signal after the noise reduction processing. The biological information which is a detection target of the biological information detecting device of the present embodiment is not limited to the pulse wave (pulse rate), and the biological information detecting device may be a device for detecting biological information (for example, oxygen saturation in the blood, body temperature, and heart rate, and the like) in addition to the pulse wave.

Here, the light-transmissive member 50 of the biological information detecting device of the present embodiment may have a curved surface-like convex portion 52. That is, the convex portion 52 in the present embodiment may have any shape that relatively protrudes compared to a peripheral region so as to appropriately apply the pressing force, and can be realized by using a curved surface shape as shown in FIG. 1A in a narrow sense.

Figure 5:
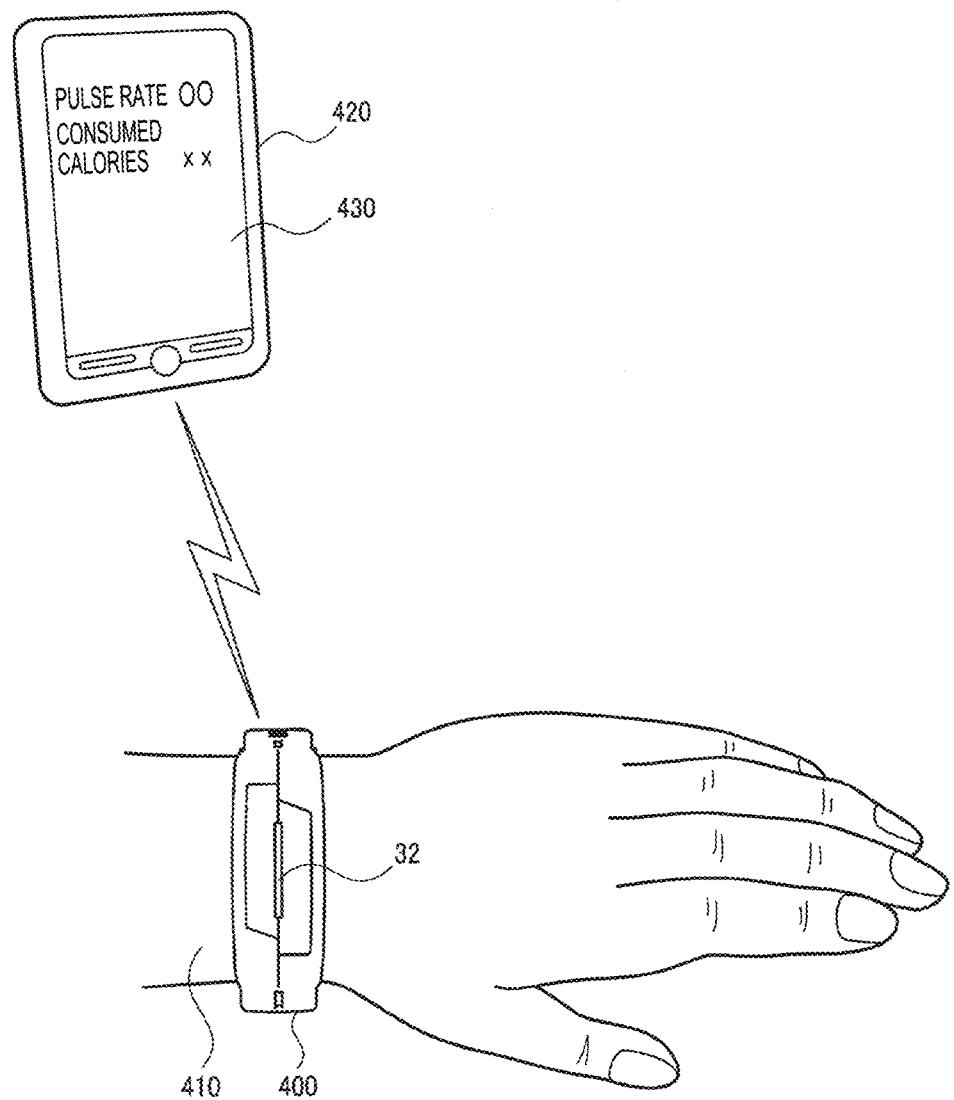
FIG. 5 is a view illustrating installation of the biological information detecting device and communication between a terminal device and the biological information detecting device.

FIG. 5 is a view illustrating installation of a biological information detecting device 400 and communication between a terminal device 420 and the biological information detecting device. As shown in FIG. 5, a user as a subject installs the biological information detecting device 400 on a wrist 410 like a watch. As shown in FIG. 4, the sensor portion 40 is provided on a surface of the case portion 30 on the subject. Accordingly, when the biological information detecting device 400 is installed, the convex portion 52 of the sensor portion 40 applies a pressing force by coming into contact with the surface of the skin of the wrist 410. In this state, the light emitting portion 150 of the sensor portion 40 emits light and the first light receiving portion 140 and the second light receiving portion 141 receive reflected light, and thereby, biological information such as a pulse wave is detected.

The biological information detecting device 400 and the terminal device 420 are communicably connected to each other, and therefore, it is possible to exchange data. The terminal device 420 is a portable communication terminal such as a smart phone, a mobile phone, and a feature phone. Alternately, the terminal device 420 may be an information processing terminal such as a tablet type computer. Proximity wireless communication such as Bluetooth (registered trade name) may be employed as a communication connection between the biological information detecting device 400 and the terminal device 420. It is possible to display various information pieces such as the pulse rate or consumed calories on a display portion 430 (LCD or the like) of the terminal device 420 by communicably connecting the biological information detecting device 400 and the terminal device 420 to each other in this manner. That is, various information pieces which are obtained based on the detection signals of the sensor portion 40 can be displayed thereon. Calculation processing of information such as the pulse rate or the consumed calories may be performed in the biological information detecting device 400, or at least one part of the processing may be performed in the terminal device 420.

The light emitting window portion 32 is provided on the biological information detecting device 400 and a user is notified of various information pieces through emission of light (lighting and flashing) from the light emitting portion for notification. For example, when the body enters a fat burning zone or when the fat burning zone ends, the user is notified of this information by the emission of light of the light emitting portion through the light emitting window portion 32. In addition, when the terminal device 420 receives an email or the like, the biological information detecting device 400 is notified of the information from the terminal device 420. Then, the user is notified of the reception of the email or the like through emission of light in the light emitting portion of the biological information detecting device 400.

In this manner, in FIG. 5, no display portion such as an LCD is provided in the biological information detecting device 400 and information, of which it is necessary to notify a user with characters, figures, or the like, is displayed on the display portion 430 of the terminal device 420. In this manner, in FIG. 5, miniaturization of the biological information detecting device 400 is realized by notifying a user of a minimum amount of necessary information through emission of light from the light emitting portion without providing any display portion such as an LCD. In addition, it is also possible to improve the aesthetic appearance of the biological information detecting device 400 by not providing the display portion in the biological information detecting device 400.

2.2 Functional Block Diagram

Figure 6:
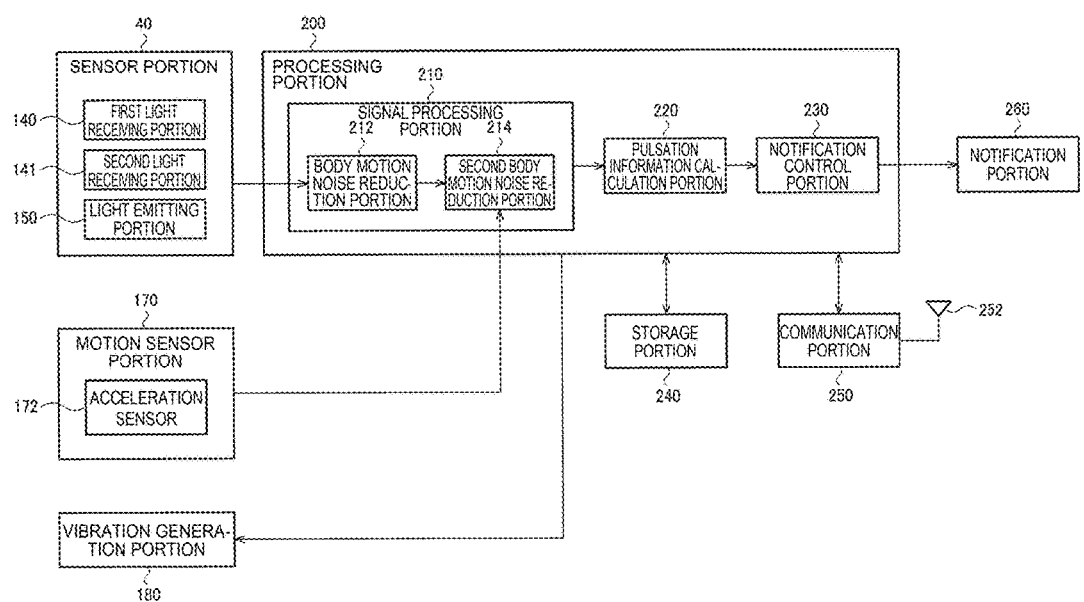
FIG. 6 is a functional block diagram of the biological information detecting device.

FIG. 6 is a functional block diagram of a biological information detecting device of the present embodiment. In FIG. 6, the biological information detecting device includes the sensor portion 40, a motion sensor portion 170, a vibration generation portion 180, the processing portion 200, a storage portion 240, a communication portion 250, an antenna 252, and a notification portion 260. The biological information detecting device of the present embodiment is not limited to the configuration of FIG. 6, and it is possible to perform various modifications, for example, omitting a part of constituents, replacing the constituents with other constituents, and adding other constituents.

The sensor portion 40 detects biological information such as a pulse wave and includes the first light receiving portion 140, the second light receiving portion 141, and the light emitting portion 150. However, the sensor portion 40 may have three or more light receiving portions. Here, an example in which the light emitting portion 150 shares a plurality of light receiving portions as will be described later is shown using FIGS. 1A to 2B or the like. However, the number of light emitting portions is not limited to one, and two or more light emitting portions may be provided.

A pulse wave sensor (photoelectric sensor) is realized by the first light receiving portion 140, the second light receiving portion 141, the light emitting portion 150, and the like. In the case of FIG. 6, a first pulse wave sensor is realized by the first light receiving portion 140 and the light emitting portion 150, and a second pulse wave sensor is realized by the second light receiving portion 141 and the light emitting portion 150. The sensor portion 40 outputs signals, which are detected by a plurality of pulse wave sensors, as detection signals (pulse wave detection signals).

The motion sensor portion 170 outputs a body motion detection signal which is a signal that changes in accordance with the body motion based on sensor information pieces of various motion sensors. The motion sensor portion 170 includes, for example, an acceleration sensor 172 as the motion sensor. The motion sensor portion 170 may have a pressure sensor, a gyro sensor, or the like as the motion sensor.

The processing portion 200 performs various kinds of signal processing or control processing by, for example, using the storage portion 240 as a working region. For example, it is possible to realize the processing using a processor such as CPU or a logic circuit such as ASIC. The processing portion 200 includes a signal processing portion 210, a pulsation information calculation portion 220, and a notification control portion 230.

The signal processing portion 210 performs various kinds of signal processing (filtering processing or the like), and for example, the signal processing is performed with respect to a pulse wave detection signal from the sensor portion 40, body motion detection signal from the motion sensor portion 170, or the like.

For example, the signal processing portion 210 includes a body motion noise reduction portion 212 and a second body motion noise reduction portion 214. The body motion noise reduction portion 212 performs body motion noise reduction processing that reduces (removes) a body motion noise, which is a noise caused by body motion, from a first detection signal based on a second detection signal among pulse wave detection signals. In addition, the second body motion noise reduction portion 214 performs second body motion noise reduction processing that reduces the body motion noise from the first detection signal based on a body motion detection signal from the motion sensor portion 170. Specifically, a spectrum subtraction method may be used for the body motion noise reduction processing in the body motion noise reduction portion 212 and an adaptive filter or the like may be used for the second body motion noise reduction processing in the second body motion noise reduction portion 214. The processing in the body motion noise reduction portion 212 and the second body motion noise reduction portion 214 will be described later in detail. In FIG. 6, a configuration in which the second body motion noise reduction processing is preformed in the second body motion noise reduction portion 214 after the body motion noise reduction processing in the body motion noise reduction portion 212 is shown. However, various modifications can be made, for example, including reversing the processing order or the like.

The pulsation information calculation portion 220 performs calculation processing of pulsation information based on a signal from the signal processing portion 210 or the like. The pulsation information is, for example, information such as a pulse. Specifically, the pulsation information calculation portion 220 performs frequency analysis processing such as FFT with respect to the pulse wave detection signal after the noise reduction processing in the body motion noise reduction portion 212 and the second body motion noise reduction portion 214, obtains a spectrum, and performs processing of setting a representative frequency to a frequency of a heartbeat in the obtained spectrum. A value, which is obtained by multiplying 60 by the obtained frequency, becomes a pulse rate (heart rate) which is generally used. The pulsation information is not limited to the pulse rate itself, and may be, for example, various other information pieces (for example, a frequency or cycle of a heartbeat) indicating the pulse rate. In addition, the pulsation information may be information indicating the state of the pulsation, and for example, a value indicating a blood volume may be used as the pulsation information.

The notification control portion 230 controls notification portion 260. The notification portion 260 (notification device) notifies a user of various information pieces by controlling the notification control portion 230. It is possible to use the light emitting portion for notification as the notification portion 260, for example. In this case, the notification control portion 230 controls lighting, flashing, or the like of the light emitting portion by controlling an electrical current flowing in an LED. The notification portion 260 may be a display portion such as an LCD, a buzzer, or the like.

In addition, the notification control portion 230 controls the vibration generation portion 180. The vibration generation portion 180 notifies a user of various information pieces through vibration. The vibration generation portion 180 can be realized using a vibration motor (vibrator), for example. The vibration motor generates a vibration by rotating an eccentric spindle, for example. Specifically, the motor itself is made swung by attaching the eccentric spindle to both ends of a driving axis (rotor axis). The vibration of the vibration generation portion 180 is controlled by the notification control portion 230. The vibration generation portion 180 is not limited to such a vibration motor and various modifications can be made thereto. For example, the vibration generation portion 180 may be realized using a piezoelectric element or the like.

For example, a notification of starting up when a power source is turned on, a notification of success in detecting an initial pulse wave, a warning when a state in which the pulse wave cannot be detected continues for a certain time, a notification during a movement of the fat burning zone, a warning when a battery voltage drops, a notification of a wake-up alarm, and a notification of an email, a phone call, or the like from a terminal device such as a smart phone can be performed using the vibration generated by the vibration generation portion 180. These information pieces may be notified by the light emitting portion for notification, or may be notified by both the vibration generation portion 180 and the light emitting portion.

The communication portion 250 performs communication processing with the external terminal device 420 as described in FIG. 5. For example, processing of wireless communication such as Bluetooth (registered trade name) or the like in compliance with the standard is performed. Specifically, the communication portion 250 performs reception processing of signals from the antenna 252 or a transmission processing of signals to the antenna 252. The function of the communication portion 250 can be realized using a processor for communication or a logic circuit such as ASIC.

2.3 Configuration Example of Sensor Portion

2.3.1 Overall Configuration Example of Sensor Portion

Figure 7:
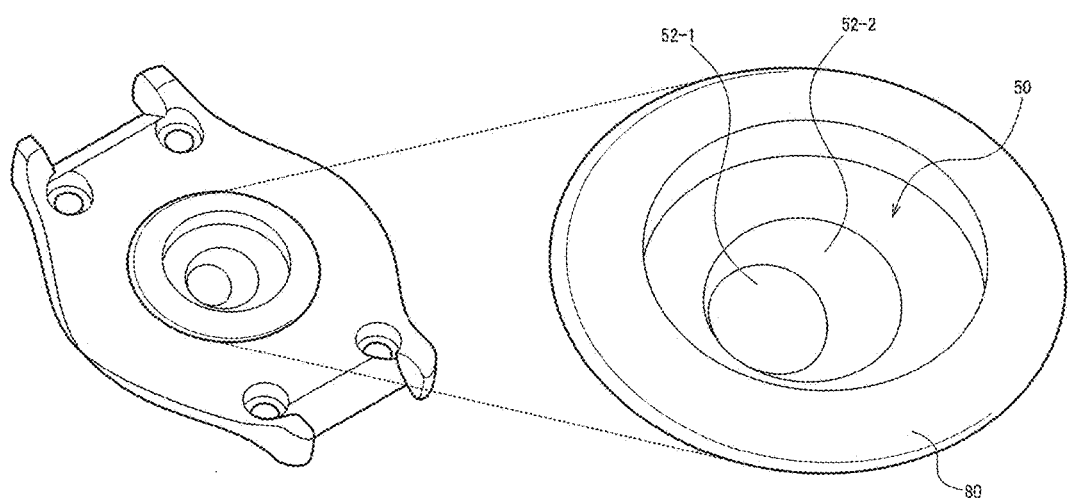
FIG. 7 is a perspective view showing the appearance of a sensor portion.

A detailed configuration example of a sensor portion 40 is shown in FIGS. 1A, 1B, and 7. FIG. 7 is a perspective view of the sensor portion 40, FIG. 1A is a cross-sectional view of the sensor portion 40, and FIG. 1B is a plan view showing a disposition of the light emitting portion 150, the first light receiving portion 140, and the second light receiving portion 141 on a substrate 160. FIG. 1B corresponds to a plan view when observed in a direction (direction of DR2) from a subject to the biological information detecting device in an installed state in FIG. 1A.

The sensor portion 40 has the first light receiving portion 140, the second light receiving portion 141, and the light emitting portion 150. The first light receiving portion 140, the second light receiving portion 141, and the light emitting portion 150 are mounted on the substrate 160 (sensor substrate). The first light receiving portion 140 and the second light receiving portion 141 receive light (reflected light, transmitted light, or the like) from a subject. The light emitting portion 150 emits light with respect to the subject. For example, if the light emitting portion 150 emits light to the subject and the light is reflected by the subject (blood vessel), the first light receiving portion 140 and the second light receiving portion 141 receive and detect the reflected light.

The first light receiving portion 140 and the second light receiving portion 141 can be realized using, for example, a light receiving element such as a photodiode. The light emitting portion 150 can be realized using, for example, a light emitting element such as an LED. For example, the first light receiving portion 140 and the second light receiving portion 141 can be realized using a p-n junction diode element which is formed on a substrate of a semiconductor. In this case, an angle limiting filter for restricting a light receiving angle, or a wavelength limiting filter for limiting a wavelength of light incident on a light receiving element may be formed on the diode element.

For example, in the case of a pulse monitor, light from the light emitting portion 150 progresses inside a subject, and is diffused or scattered in the epidermis, the dermis, the subcutaneous tissue, or the like. Then, the light reaches blood vessels (portion to be detected) and is reflected from the blood vessels. At this time, a portion of light is absorbed by the blood vessels. Then, the absorption rate of light changes in the blood vessels due to the pulse and the amount of reflected light also changes. Therefore, the first light receiving portion 140 receives the reflected light and detects the change in the amount of the light such that it is possible to detect the pulse rate as biological information or the like.

A light shielding member 70 (light shielding wall 100) is provided between the first and second light receiving portions 140 and 141 and the light emitting portion 150. In the disposition shown in FIG. 1A, the light shielding wall 100 is provided between the first light receiving portion 140 and the light emitting portion 150. The light shielding member 70 shields light from the light emitting portion 150 so that the light is not directly incident on the first light receiving portion 140 and the second light receiving portion 141.

In addition, a throttle portion which is not shown in the drawing may be provided in the sensor portion 40. The throttle portion restricts light from a subject or light from the light emitting portion 150 in an optical path between the subject and the sensor portion 40. The throttle portion is, for example, provided between the light-transmissive member 50 and the sensor portion 40. The throttle portion may also be provided between the light-transmissive member 50 and a subject or in the light-transmissive member. In addition, the light shielding member 70 and the throttle portion may be integrally formed by subjecting metal to sheet metal working, for example.

The light-transmissive member 50 is provided on a surface on the side of the biological information detecting device coming into contact with a subject and transmits light from the subject. In addition, the light-transmissive member 50 comes into contact with the subject at the time of measuring the biological information of the subject. For example, the convex portion 52 (detection window) of the light-transmissive member 50 comes into contact with the subject. It is desirable that the shape of the surface of the convex portion 52 be a curved surface shape (spherical surface shape). However, the shape of the surface of the convex portion 52 is not limited thereto and various shapes can be employed. In addition, the light-transmissive member 50 may be transparent with respect to a wavelength of light from the subject, and a transparent material or a colored material may be used.

2.3.2 Distance Between Light Emitting Portion and Light Receiving Portion

Figure 8:
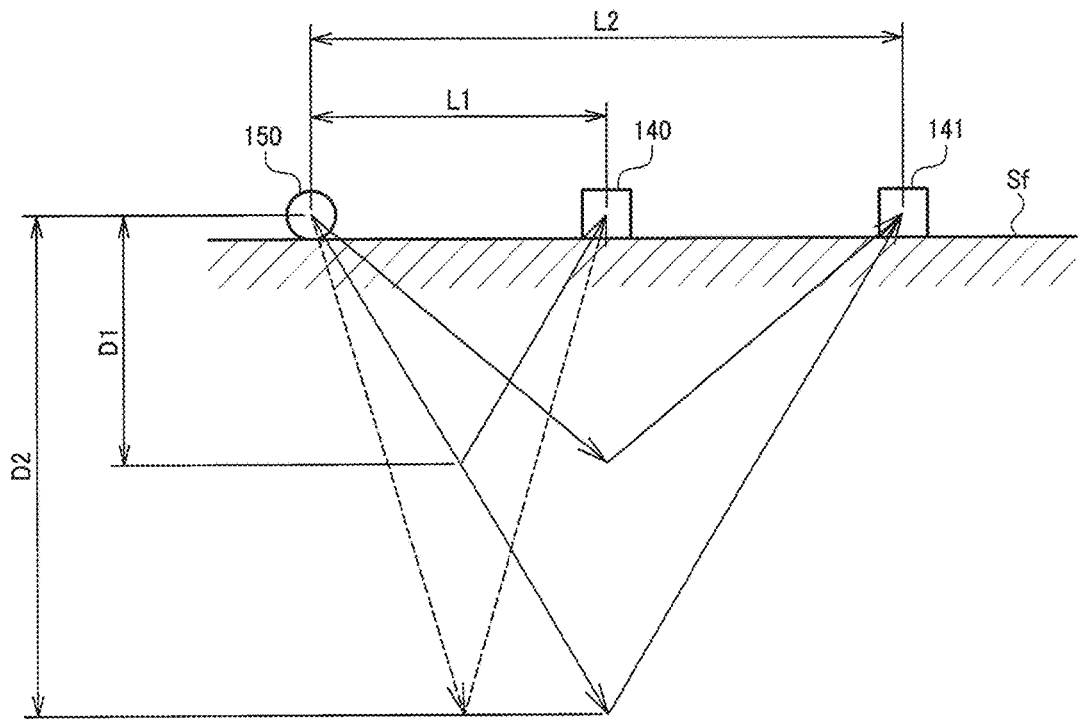
FIG. 8 is a view illustrating an influence of the distance between the light emitting portion and the light receiving portions on permeation depth of light.

Next, a distance L1 between the light emitting portion 150 and the first light receiving portion 140 and a distance L2 between the light emitting portion 150 and the second light receiving portion 141 will be described. FIG. 8 is a view illustrating the influence of the distance between the light emitting portion and the light receiving portions on permeation depth of light. The light emitting portion 150 and the first light receiving portion 140 come into contact with a skin surface Sf of the wrist of a user and the light emitting portion 150 and the second light receiving portion 141 come into contact with the skin surface Sf of the wrist of the user. Here, the two light receiving portions share the light emitting portion 150 as described above. In reality, the light-transmissive member 50 comes into contact with the skin surface Sf as described above. However, the light-transmissive member 50 is omitted in FIG. 8 to simplify the description.

It is known that sensitivity with respect to a deep portion in a living body becomes lower compared to sensitivity with respect to a shallow portion as the distance between the light emitting portion and the light receiving portion is shorter. That is, the intensity of light emitted from the light emitting portion 150 which is reflected at a position of a depth D1 in a biological tissue and reaches the first light receiving portion 140 is stronger than the intensity of light emitted from the light emitting portion 150 which is reflected at a position of a depth D2 which is deeper than the depth D1 and reaches the first light receiving portion 140. In contrast, although the intensity of light emitted from the light emitting portion 150 which is reflected at the position of the depth D1 and reaches the second light receiving portion 141 is stronger than the intensity of light emitted from the light emitting portion 150 which is reflected at the position of the depth D2 and reaches the second light receiving portion 141, there is no such a great difference between the intensities that is caused in the first light receiving portion 140. For this reason, the first light receiving portion 140 is suitable for measuring a pulse wave in blood vessels at a shallower position than that of the second light receiving portion 141.

Figure 9:
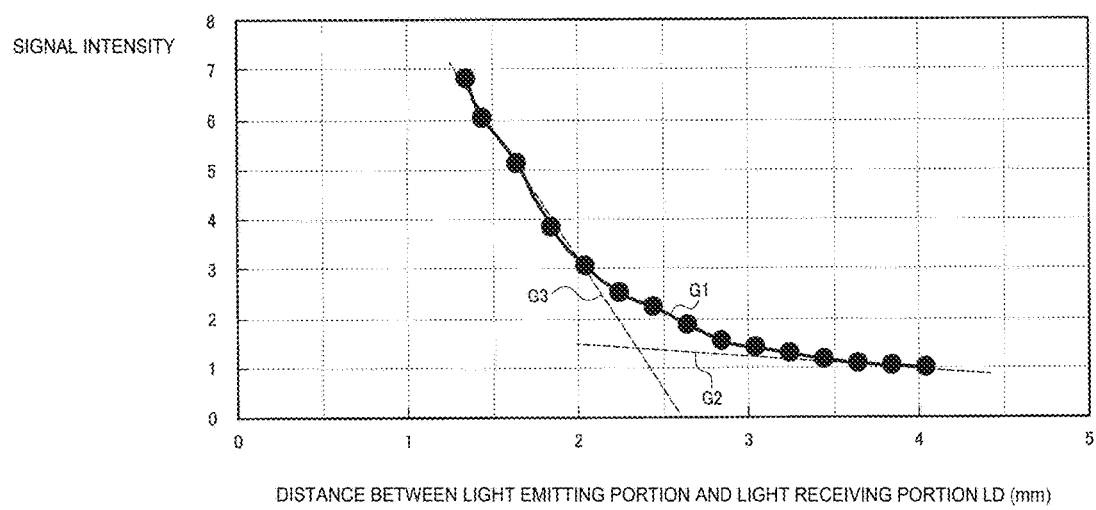
FIG. 9 is a view showing a relationship between signal intensity of a detection signal and the distance between the light emitting portion and the light receiving portions.

FIG. 9 is a view showing the relationship between signal intensity and a distance LD between the light emitting portion 150 and the light receiving portion. The distance LD between the light emitting portion 150 and the light receiving portion is, for example, a distance between the light emitting portion 150 and a central position (representative position) of the light receiving portion. For example, when the light receiving portion has a rectangular shape (substantially rectangular shape), the position of the light receiving portion is in a central position of the rectangular shape. In addition, when the light emitting portion 150 has a lens portion 151 as shown in FIG. 1A or the like, the position of the light emitting portion 150 is, for example, in a central position (position of an LED chip) of the lens portion 151.

As is clear from FIG. 9, as the distance LD between the light emitting portion 150 and the light receiving portion becomes shorter, the signal intensity of a detection signal becomes stronger, and therefore, the detection performance including sensitivity is improved. Accordingly, it is desirable that the distance LD between the light emitting portion 150 and the first light receiving portion 140, which mainly detects a pulse signal, be shorter.

In this case, as shown in FIG. 9, it is desirable that the distance between the first light receiving portion 140 and the light emitting portion 150 be LD<3 mm. For example, as is clear from a tangential line G2 on a side of a characteristic curve G1 of FIG. 9 on which the distance between the first light receiving portion and the light emitting portion is long, the characteristic curve G1 is saturated in a range of LD>=3 mm. On the contrary, in a range of LD<3 mm, the signal intensity is greatly increased as the distance LD becomes shorter. Accordingly, it is desirable that LD>3 mm be satisfied in this sense.

In the sensor portion 40 of the present embodiment shown in FIGS. 2A and 2B, the distance L1 between the light emitting portion 150 and the first light receiving portion 140 is, for example, about L1=1.0 mm to 3.0 mm.

Figure 10:
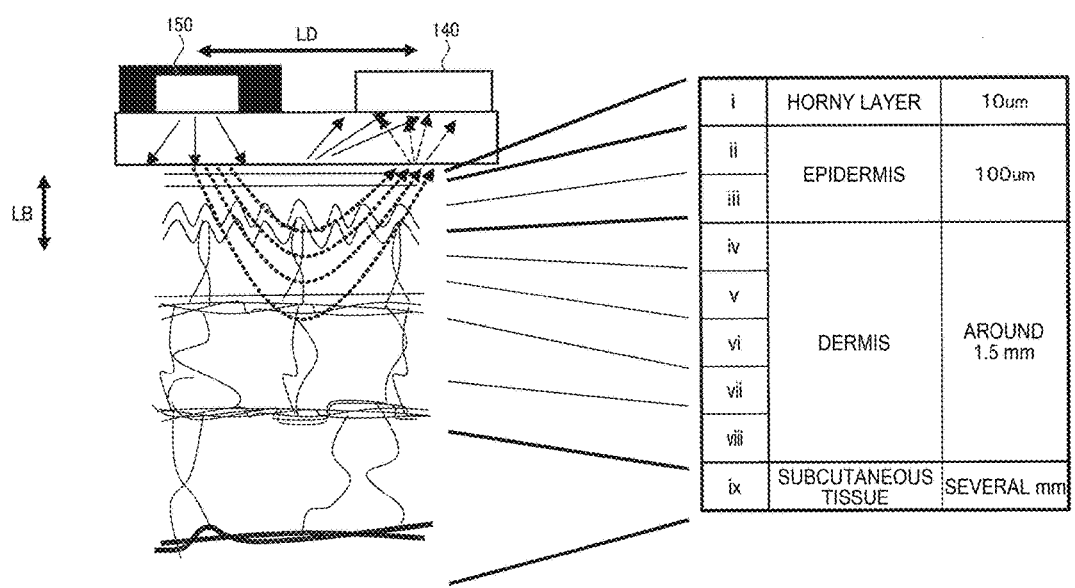
FIG. 10 is a view illustrating the relationship between a measurement distance in a depth direction and the distance between the light emitting portion and the light receiving portions.

In addition, there is also a lower limit value for the distance LD, and it is not desirable that the distance LD be too short. FIG. 10 is a schematic view showing a state in which light emitted from the light emitting portion 150 is reflected and scattered in a living body and a part of the reflected or scattered light is received by the light receiving portion. In this case, light from the light emitting portion 150 is diffused or scattered in the blood vessels of a subject or the like, the diffused or scattered light is incident on the light receiving portion, and a pulse wave is detected. In FIG. 10, in general, a relationship of LD=2×LB is satisfied between the distance LD between the light emitting portion 150 and the light receiving portion, and a measurement distance LB in a depth direction. For example, a measurement limit distance using a light detection unit configured to include the light emitting portion 150 and the light receiving portion which are separated by a distance LD is about LB=LD/2. Moreover, there is no blood vessel which becomes a detection object of a pulse wave within a range where the distance LB is 100 micrometers to 150 micrometers. Accordingly, when the distance LD becomes LD<=2×LB=2×100 micrometers to 2×150 micrometers=0.2 mm to 0.3 mm, it is expected that the detection signal of the pulse wave may become extremely small. That is, when the distance LD becomes short, the measurement distance LB also becomes short in a depth direction. Therefore, if there is no detection object within a range of the distance LB, the detection signal becomes extremely small. That is, the shorter the distance LD is, the better the detection performance is, but there is a limitation and a lower limit value. In the present embodiment, the distance L1 is set to about L1>=1.0 mm since it is necessary to detect a pulse signal in the first light receiving portion 140 with sufficient intensity. That is, it is desirable that the distance L1 be 1.0 mm<=L1<=3.0 mm.

On the contrary, the distance L2 between the light emitting portion 150 and the second light receiving portion 141 may be set such that the sensitivity with respect to a pulse signal is lower than that of the first light receiving portion 140 and the sensitivity with respect to a body motion noise is higher than that of the first light receiving portion 140. For example, when L2<1.0 mm or 3.0 mm<L2, the degree of the pulse signal is decreased and the degree of the body motion noise is increased (an MN ratio is decreased), compared to the first light receiving portion 140 having a range of 1.0 mm<=L1<=3.0 mm.

However, in the second light receiving portion 141, the MN ratio (where M represents a pulse signal, N represents a noise, and the MN ratio is a ratio (generally, SN ratio) of the pulse signal to the noise) of the detection signal may be sufficiently small compared to the MN ratio of the detection signal of the first light receiving portion 140. That is, a point in which the value of L2 is changed with respect to L1 may be emphasized rather than a point of setting the distance, such as L2<1.0 mm or 3.0 mm< L2, as an absolute value, so as to be able to create a difference between the first and second detection signals to some extent (for example, to the extent that noise reduction processing can be performed through a spectrum subtraction method to be described later).

That is, the pulse component may be included in the second detection signal from the second light receiving portion 141 to some extent as long as it is enough to have a smaller MN ratio than that of the first detection signal. In other words, L2 may be within a range of 1.0 mm<=L2<=3.0 mm.

Here, a relationship such as L2>2×L1 may be satisfied as a relationship between L1 and L2 for creating a difference between the first and second detection signals. In this case, if L1 is 1.0 mm, L2 may be 2.5 mm or the like since L2 is greater than 2.0 mm, and the pulse signal is detected with a certain degree of intensity. Moreover, it is possible to satisfy the condition that the MN ratio of the second detection signal be smaller than that of the first detection signal for which a smaller distance L1 is set.

When the body motion noise is relatively increased in the second light receiving portion 141, L2 may be set to be extremely small as described above. That is, the distance between each of the light receiving portions and the light emitting portion 150 may be determined using a relationship of L2<L1, for example, L2<L1/2. However, in some cases, it is difficult to set L1 or L2 to an extremely small value in consideration of the necessity of providing the light shielding wall 100 or the like in order to shield direct light from the light emitting portion 150 to each of the light receiving portions. For example, in a case that L1=1.0 mm, it is necessary to satisfy L2<0.5 mm or the like, and therefore, it could be difficult to dispose each of the components in terms of space. Hereinafter, an example in which L2>L1 will be mainly described by considering such a point. However, a relationship of L2<L1 may be set depending on the situation.

Various disposition techniques that satisfy the above-described relationship of the distance can be considered. For example, the biological information detecting device may have at least one light emitting portion (light emitting portion 150) which emits light with respect to a subject, and the first light receiving portion 140 may be disposed between the light emitting portion 150 and the second light receiving portion 141.

An example of such disposition is shown in the above-described FIGS. 2A and 2B. In this case, L1 and L2 become the distances shown in FIG. 2A or the like. Here, L1 and L2 have a relationship in which L2>2×L1, and therefore, the above-described relationship is satisfied if L1 is set to 1.0 mm to 3.0 mm, for example.

As described above, in the biological information detecting device according to the present embodiment, it is possible to perform various modifications of the relationship between L1 and L2. However, in a narrow sense, when the distance between the light emitting portion 150 and the first light receiving portion 140 is set to L1 and the distance between the light emitting portion 150 and the second light receiving portion 141 is set to L2, L2>L1 is satisfied, and more specifically, L2>2×L1 is satisfied.

In addition, when using a specific numerical value, L1 may satisfy 1 mm<=L1<=3 mm and L2 may satisfy 2 mm<=L2. However, as described above, if a relative relationship with L1 is to be emphasized, it is necessary that the condition of L2 satisfy not only 2 mm<=L2, but also the relative relationship. For example, L2> L1 and L2>=2 mm may be satisfied. Alternatively, L2>2×L1 and L2>=2 mm may be satisfied under a strict condition.

2.3.3 Height of Light-Transmissive Member

In addition, it is known that sensitivity with respect to a pulse signal or a body motion noise also changes due to a pressing force with respect to a subject.

Figure 11:
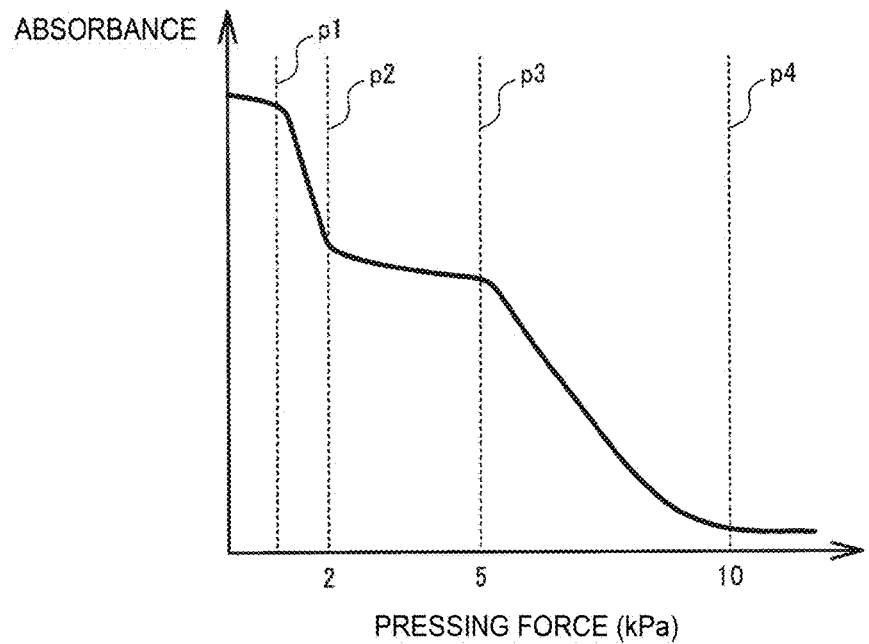
FIG. 11 is a view illustrating change in absorbance with respect to a pressing force.

FIG. 11 is a view illustrating change in absorbance with respect to a pressing force. The horizontal axis indicates the pressing force and the longitudinal axis indicates the absorbance. If the pressing force changes, affected blood vessels change. Blood vessels which are the most likely to be affected by the pressing force, that is, blood vessels which are affected by the lowest pressing force are capillaries. In the example shown in FIG. 11, the amount of change in the absorbance is great when the pressing force exceeds p1, which means that the capillaries start to collapse due to the pressing force. The absorbance gently changes when the pressing force exceeds p2, which means that the capillaries have almost completely collapsed (being closed). An artery is a blood vessel which is affected after the capillaries are. The amount of change in the absorbance is again great when the pressing force is further increased to exceed p3, which means that an artery starts to collapse due to the pressing force. The absorbance gently changes when the pressing force exceeds p4, which means that the artery has almost completely collapsed (being closed).

In the present embodiment, the second light receiving portion 141 increases the proportion of the body motion noise by detecting a signal corresponding to capillaries and the first light receiving portion 140 increases the proportion of the pulse signal by measuring a signal (pulse signal) corresponding to an artery. For this reason, the pressing force in the second light receiving portion 141 is designed to be within a range of p1 to p2 and the pressing force in the first light receiving portion 140 is designed to be within a range of p3 to p4. It is desirable that the difference between the pressing force of the first light receiving portion 140 and the pressing force of the second light receiving portion 141 be, for example, 2.0 kPa to 8.0 kPa.

Figure 12:
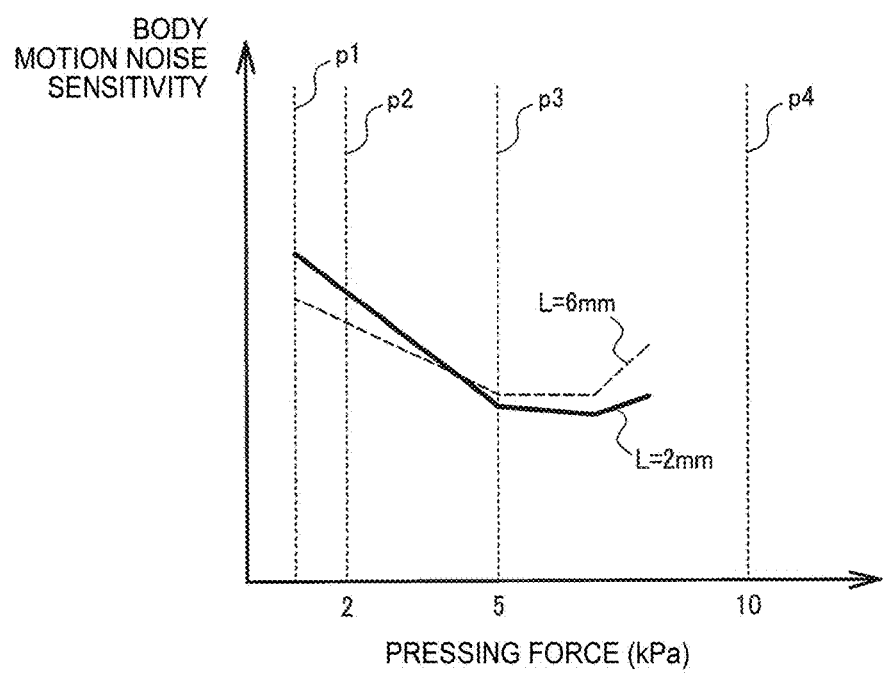
FIG. 12 is a view illustrating change in sensitivity of a body motion noise with respect to the pressing force.

FIG. 12 is a view illustrating change in sensitivity of a body motion noise with respect to the pressing force. In FIG. 12, an example of a distance L from a light emitting portion to a light receiving portion being 2 mm and an example thereof being 6 mm are shown together. In all examples of the distance L being 2 mm and 6 mm, as a general tendency, the lower the pressing force is, the higher the noise sensitivity is, and the higher the pressing force is, the lower the noise sensitivity is. It is considered that this is because blood flowing through capillaries is easily moved by body motion, and therefore, a noise due to body motion is easily included in light which is reflected by the capillaries existing at a position comparatively shallow in a biological tissue.

Figure 13A:
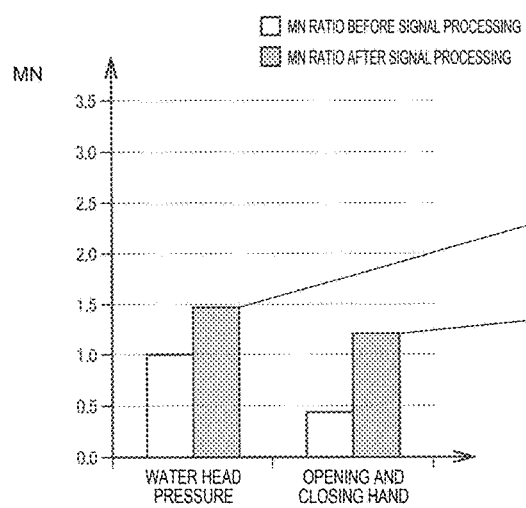
FIG. 13 shows views illustrating a degree of improvement in an MN ratio (SN ratio) due to noise reduction processing, between a case of providing a difference in the pressing force and a case of not providing the same.

In addition, FIG. 13A is a view showing a change in an MN ratio of a first detection signal before and after body motion noise reduction processing in a case of providing a difference only in the distances L1 and L2 between the light emitting portion 150 and the light receiving portions without providing any difference between the pressing force of the first light receiving portion 140 and the pressing force of the second light receiving portion 141. Here, the degree of a reduced body motion noise corresponding to movements, such as changing a water load and opening and closing the hand, which are performed as movements of a user which generate body motion noise is measured. The movement of changing the water load is, for example, a movement of changing the height of a measurement position, and specifically, it is possible to realize the movement by raising or lowering the arm. The opening and closing of the hand can be realized by movements in which a state where every finger is bent so as to clench the fist and a state where fingers are firmly stretched to open the hand are alternately performed.

Figure 13B:
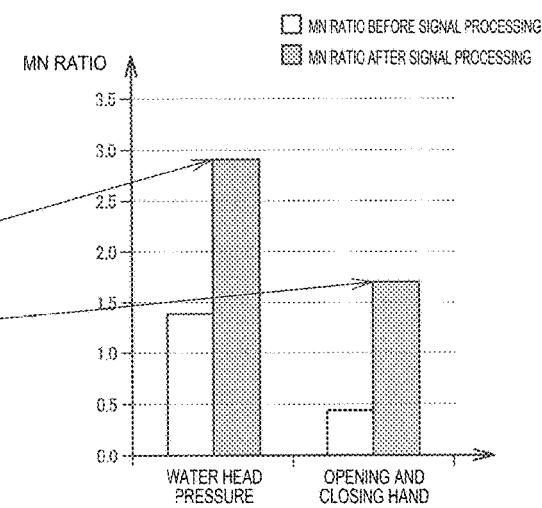

As is clear from FIG. 13A, it is possible to confirm the effect of reducing the body motion noise by only providing a difference in the distance. On the contrary, FIG. 13B is a view showing a change in an MN ratio of a first detection signal before and after body motion noise reduction processing in a case of providing a difference in the distances L1 and L2 between the light emitting portion 150 and the light receiving portions and also providing a difference between the pressing force of the first light receiving portion 140 and the pressing force of the second light receiving portion 141. As is clear from the comparison between FIGS. 13A and 13B, it can be seen that the effect of reducing the body motion noise is improved by also providing a difference in the pressing force. Accordingly, the case of providing both the difference in the distance and the difference in the pressing force will be described herein.

That is, at the time of measuring the biological information of a subject, when the pressing force of the light-transmissive member 50 at a position or in a region corresponding to the first light receiving portion 140 is set to P1 and the pressing force of the light-transmissive member 50 at a position or in a region corresponding to the second light receiving portion 141 is set to P2, P1>P2 is satisfied. In this manner, it is possible to provide a difference in the characteristics between a first detection signal from the first light receiving portion 140 and a second detection signal from the second light receiving portion 141.

Specifically, providing a difference in the pressing force may be realized using a difference in the height of the light-transmissive member 50 coming into contact with a subject. As described above, the pressing force in the first light receiving portion 140, which mainly detects a pulse signal, is set to be high and the pressing force in the second light receiving portion 141 is set to be lower than that in the first light receiving portion 140. For this reason, the height h1 of the light-transmissive member at a position or in a region corresponding to the first light receiving portion 140 may be set to be high compared to the height h2 of the light-transmissive member at a position or in a region corresponding to the second light receiving portion 141.

This is because it is possible to set the pressing force, which corresponds to the first light receiving portion 140 having a high height, to be stronger than the pressing force which corresponds to the second light receiving portion 141 having a low height, when fixing a biological information detecting device to the wrist or the like under a given cuff pressure, since the light-transmissive member protrudes to the subject side as the height of the light-transmissive member becomes higher. This is shown in FIG. 14.

Figure 14:
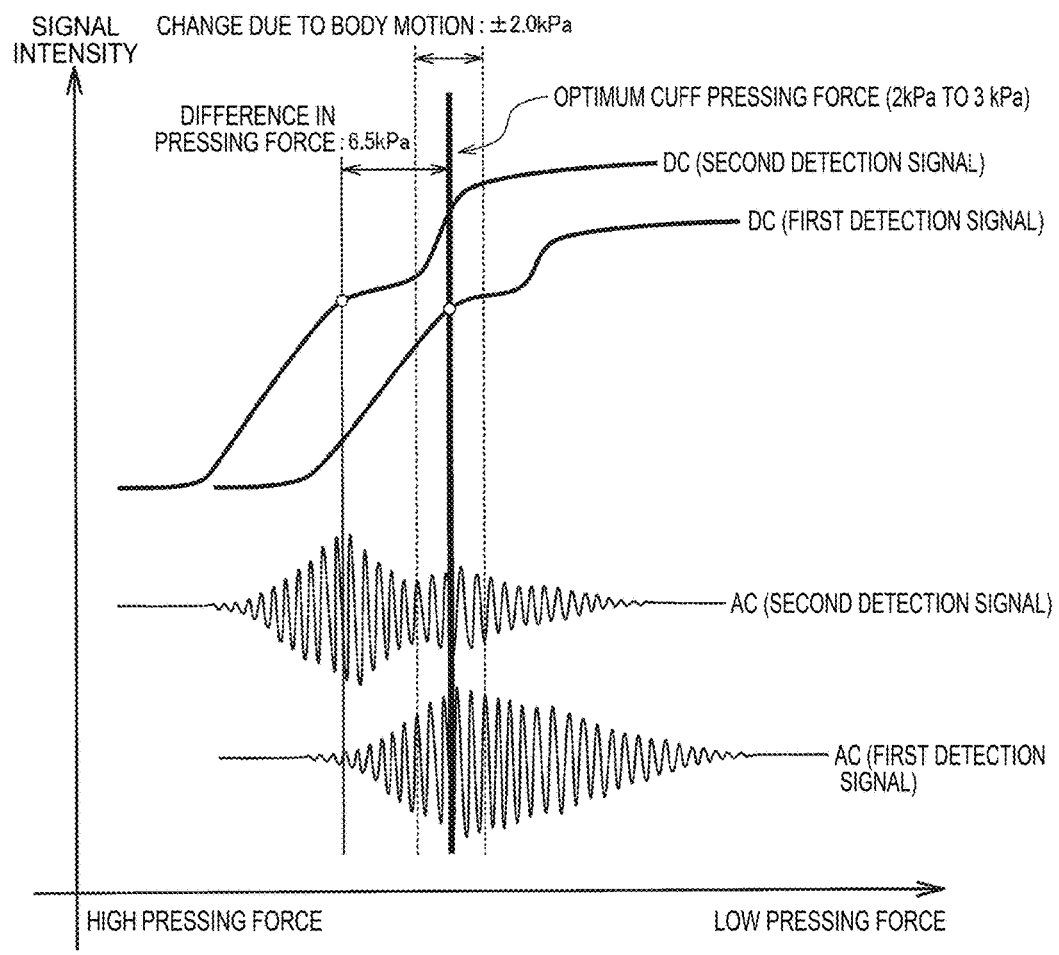
FIG. 14 is a view showing the relationship between a DC component and an AC component, which are detected by each light receiving portion, and a cuff pressing force.

The horizontal axis of FIG. 14 indicates a cuff pressing force (pressure caused by the band portion 10 in the case of the biological information detecting device shown in FIG. 3A) and the longitudinal axis of FIG. 14 indicates DC and AC components of detection signals. As can be seen from a DC signal shown on the top of FIG. 14, in the first light receiving portion 140 where the pressing force is comparatively high, a pressing force is added to a subject to some degree even in a state where the cuff pressing force is comparatively low, and therefore, the DC component is suppressed. On the contrary, the pressing force in the second light receiving portion 141 is comparatively low, and therefore, the condition of suppressing the DC component in a state where a given cuff pressure is applied is worse compared to the first detection signal. For this reason, in the range of the "optimum cuff pressing force" shown in FIG. 14, the pressing force corresponding to the first light receiving portion 140 falls in a range of p3 to p4. Thus, the noise is suppressed and the signal level of the pulse signal becomes great. In contrast, the pressing force in the second light receiving portion 141 falls in a range of p1 to p2, and therefore, the noise is not sufficiently suppressed and the proportion of the body motion noise increases.

This is also clear from the comparison with the AC component shown on the bottom of FIG. 14, and in the range of the optimum cuff pressing force, the signal level of the AC component in the first detection signal is high and the signal level of the AC component in the second detection signal is low. As described above, the pulse signal is represented by the change of the detection signal, that is, by the AC component. Therefore, FIG. 14 shows that the second light receiving portion 141 has a relatively high proportion of the body motion noise while the first light receiving portion 140 can sufficiently detect the pulse signal.

Hereinafter, the difference in the height of the light-transmissive member 50 will be described in detail using the drawings. The perspective view, the cross-sectional view, and the plan view of the sensor portion 40 are as shown in FIGS. 7, 1A, and 1B, respectively. As can be seen from FIGS. 7 and 1A, the light-transmissive member 50 has the convex portion 52 and a suitable pressing force is applied to a subject using the convex portion 52.

In the biological information detecting device according to the present embodiment, a plurality of photoelectric sensors are realized by providing a plurality of light receiving portions, and therefore, a plurality of convex portions 52 (for example, the number corresponding to the number of photoelectric sensors) may also be provided. In the example of FIG. 1A, a convex portion 52-1 is provided with respect to a first photoelectric sensor which is realized by the light emitting portion 150 and the first light receiving portion 140, and a convex portion 52-2 is provided with respect to a second photoelectric sensor which is realized by the light emitting portion 150 and the second light receiving portion 141.

At this time, in a state where the biological information detecting device is installed, when the direction (DR1 in FIG. 1A) facing a subject from the biological information detecting device is set to a height direction, the height h1 of the light-transmissive member at a position or in a region corresponding to the first light receiving portion 140 is higher than the height h2 of the light-transmissive member at a position or in a region corresponding to the second light receiving portion 141. This can also be realized by setting the height of the convex portion 52-1 to be higher than the height of the convex portion 52-2, for example. Various modifications can be made related to how the height thereof is defined. For example, the distance from a surface of the substrate 160 on which the light emitting portion 150 or the like is provided may be set to the height as shown in FIG. 1A. Alternately, the thickness of the light-transmissive member 50 itself may also be set to the height.

Alternately, a reference surface, which is provided on a side (lower side of FIG. 1A) opposite to a subject with respect to the substrate 160 and is parallel to the surface of the substrate 160, may be set in the state where the biological information detecting device is installed, and the distance from the reference surface may be set as the height of the light-transmissive member 50. The reference surface may be a surface of any member (for example, a main substrate on which the processing portion 200 is mounted) or a virtual plane.

In addition, various definitions can also be considered for the position or the region corresponding to each light receiving portion. For example, the height h1 may be a height of the light-transmissive member 50 at a representative position of the first light receiving portion 140 and the height h2 may be a height of the light-transmissive member 50 at a representative position of the second light receiving portion 141. The representative position referred to herein may use a central position of each of the light receiving portions, for example.

In this case, the central position of the first light receiving portion 140 is A1 as shown in FIG. 1B and the central position of the second light receiving portion 141 is A2. Moreover, the height of the light-transmissive member 50 in the central position A1 of the first light receiving portion 140 defines the intersection between the straight line, which extends in the DR1 direction from A1, and the surface (surface coming into contact with a subject during installation) of the light-transmissive member 50, as shown in FIG. 1A, and the height h1 of the light-transmissive member 50 in the intersection may be used. Similarly, the height of the light-transmissive member 50 in the central position A2 of the second light receiving portion 141 is h2 as shown in FIG. 1A.

Alternately, when a region including the first light receiving portion 140 and the light emitting portion 150 in a plan view seen from the subject side is set as a first region and a region including the second light receiving portion 141 and the light emitting portion 150 in a plan view seen from the subject side is set as a second region, the height h1 may be an average height of the light-transmissive member 50 in the first region and the height h2 may be an average height of the light-transmissive member 50 in the second region.

Here, the plan view seen from the subject side indicates a state in which the direction of DR2 is observed from a point of view which is set further on the subject side (DR1 side) than the light emitting portion 150 or the like in FIG. 1A, and specifically, a state of FIG. 1B. In addition, various regions containing the light emitting portion and the light receiving portion can be considered. For example, a region, which includes a light emitting portion and a light receiving portion and has a rectangular shape of which the area is minimum, may be considered. In this case, the region (first region) corresponding to the first light receiving portion 140 is R1 of FIG. 15B.

Figure 15A:
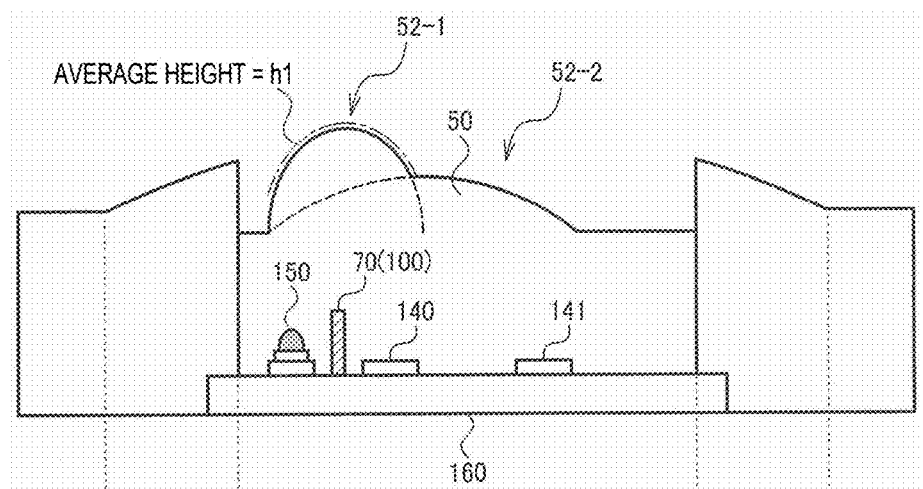
FIG. 15 shows views illustrating a region corresponding to the first light receiving portion and the height of a light-transmissive member in the region.
Figure 16A:
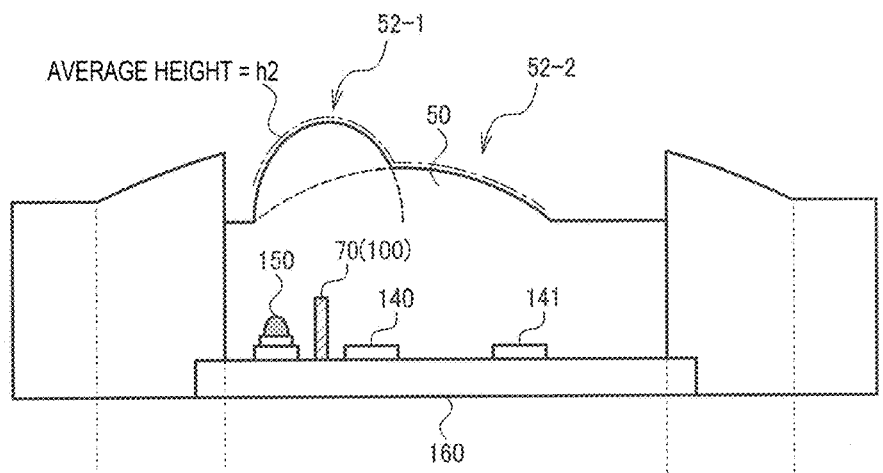
FIG. 16 shows views illustrating a region corresponding to the second light receiving portion and the height of a light-transmissive member in the region.

The height of the light-transmissive member in the region corresponding to the first light receiving portion 140 defines the intersections between straight lines, which extend in the DR1 direction from points included in R1, and the surface of the light-transmissive member 50, and can be obtained by averaging the heights of the light-transmissive member 50 in the intersections. For example, an average value of the heights of the light-transmissive member 50 in the range shown in FIG. 15A is h1. Only one cross section is shown in FIG. 15A, but the averaging of the heights in a depth direction in FIG. 15A may also be performed. Similarly, a region (second region) corresponding to the second light receiving portion 141 may be set as shown in R2 of FIG. 16B and the average height in a range shown in FIG. 16A may be set to h2.

In addition, a contact portion 80 that stabilizes a state in which the sensor portion 40 and the subject come into contact with each other may also be provided in addition to h1 and h2. Here, the contact portion is, for example, 80 as shown in FIG. 1A and is provided around the light emitting portion 150, the first light receiving portion 140, and the second light receiving portion 141 as shown in FIG. 7, for example. In the example of FIG. 7, the contact portion 80 having a circumferential shape surrounding the light emitting portion 150 or the like is shown. However, the contact portion is not limited thereto and may have a shape such as a polygonal shape. Alternately, it is not necessary to realize the contact portion 80 using a continuous shape, and the contact portion 80 (which is configured to have a plurality of arcs which do not come into contact with each other, for example) having a gap may also be used. Furthermore, as will be described later using FIG. 19B, in a case in which there are a plurality of light emitting portions, and first and second light receiving portions are disposed so as to face light emitting portions, the contact portion 80 may have a shape which surrounds all of the light emitting portion 150, the second light emitting portion 157, the first light receiving portion 140, and the second light receiving portion 141, but the contact portion is not limited thereto. For example, the contact portion 80 may be configured to have a first contact portion, which is provided around the light emitting portion 150 and the first light receiving portion 140, and a second contact portion, which is provided around the second light emitting portion 157 and the second light receiving portion 141.

It is estimated that when providing such a contact portion 80, a biological information detecting device is fixed to a subject in a state in which a pressure is (ideally) evenly applied in the contact portion 80. That is, a plane surface defined by the contact portion 80 becomes a surface representing a reference during installation of the biological information detecting device. In this case, it is possible to make the difference between a pressing force at a higher position than the surface as a reference and a pressing force at a lower position than the surface as a reference obvious.

For example, when the height of the above-described surface as a reference, that is, the height of the contact portion 80 is set to h3, it is possible to make the pressing force corresponding to h_alpha be greater than the pressing force corresponding to h_beta even if h_alpha>h_beta>h3 or h3>h_alpha>h_beta is set. However, if h_alpha>h_beta>h3 is satisfied, a pressure is more easily applied to the position corresponding to h_alpha and the position corresponding to h_beta than the contact portion 80, and therefore, the difference in the pressure does not become great. Similarly, if h3>h_alpha>h_beta is satisfied, a pressure is more easily applied to the contact portion 80 than the position corresponding to h_alpha or the position corresponding to h_beta, and therefore, the difference in the pressing force also does not become obvious.

On the contrary, when h_alpha>h3>h_beta is set, the pressure at the position of h_beta is released to the contact portion 80 whereas the pressing force is more easily applied to the position corresponding to h_alpha than the contact portion 80, and therefore, it is difficult to apply the pressing force. As a result, it is possible to make the difference in the pressing force therebetween by providing a position higher than h3 and a position lower than h3.

When applying this to the present embodiment, the height h1 corresponding to the first light receiving portion 140 corresponds to h_alpha and the height h2 corresponding to the second light receiving portion 141 corresponds to h_beta. That is, the biological information detecting device according to the present embodiment has the contact portion 80 which is provided around the light-transmissive member 50 and comes into contact with a subject at the time of measuring the biological information of the subject. As shown in FIG. 1A, when the height at a position or in a region corresponding to the contact portion 80 is set to h3, h1>h3>h2 is satisfied.

By doing this, it is possible to make the difference between the first detection signal and the second detection signal obvious. When considering h3, the reference of the height needs to be standardized with h1 and h2, and in FIG. 1A, for example, the distances with respect to the surface of the substrate 160 on which the light emitting portion 150 or the like is installed is set to h1 to h3.

2.4 Modification Example of Disposition of Light Emitting Portion and Light Receiving Portion Next, a modification example of disposition of a light emitting portion and light receiving portions on the substrate 160 will be described. In FIGS. 1A and 1B, the light emitting portion 150, the first light receiving portion 140, and the second light receiving portion 141 are arranged and installed in this order along a given direction after the first light receiving portion 140 and the second light receiving portion 141 share the light emitting portion 150. In addition, in the case of the above-described modification example in which L1>L2, the light emitting portion 150, the second light receiving portion 141, and the first light receiving portion 140 are arranged and installed in this order along a given direction.

However, the disposition of the light emitting portion 150 and the plurality of light receiving portions is not limited thereto. For example, the light emitting portion 150 may be disposed between the first light receiving portion 140 and the second light receiving portion 141. In this case, as shown in FIGS. 17A and 17B, the first light receiving portion 140, the light emitting portion 150, and the second light receiving portion 141 are arranged and installed in this order along a given direction.

Figure 17A:
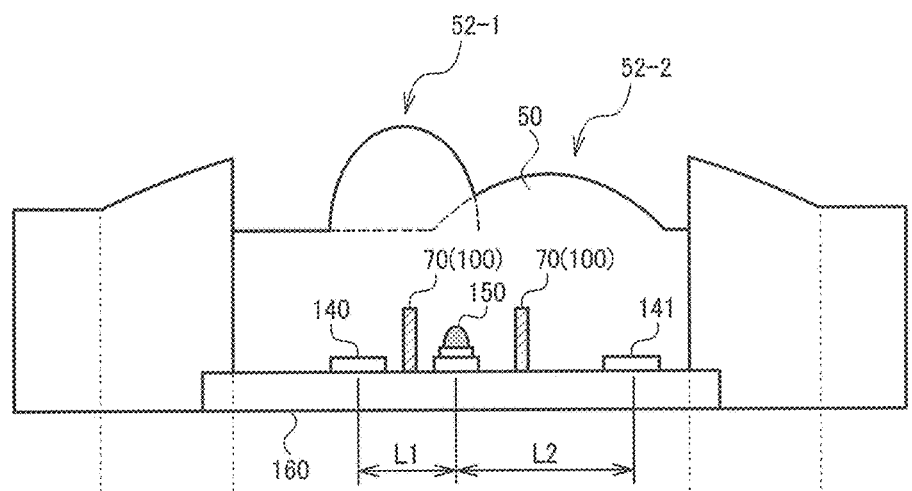
FIG. 17 shows a cross-sectional view and a plan view showing an example in which the first and second light receiving portions are disposed opposite to each other.
Figure 17B:
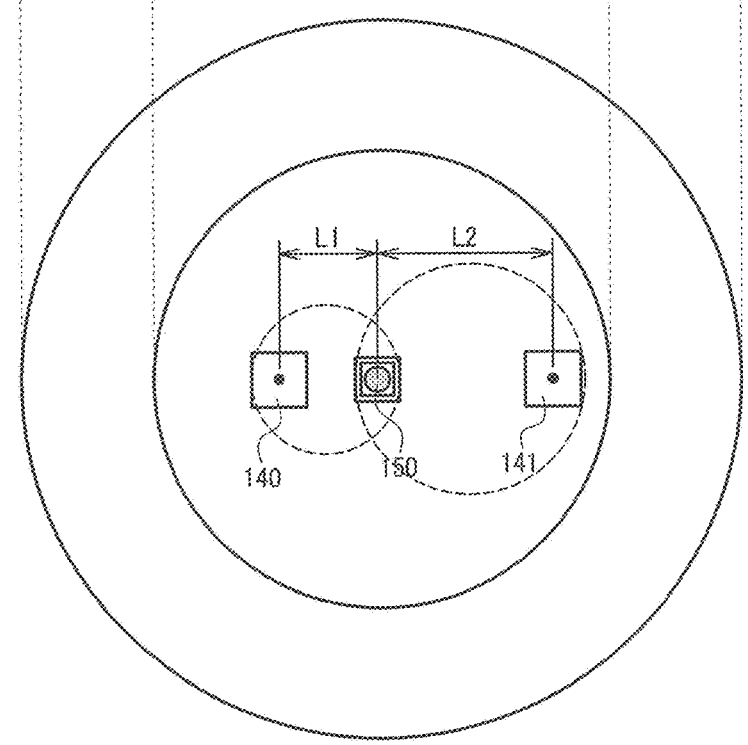

Even in this case, if the characteristics of detection signals are made to be different depending on the distance between the light emitting portion and the light receiving portions as described above, a difference may be provided between L1 and L2 as shown in FIG. 17B, and L1<L2 (L2>2×L1 in narrower sense) may be satisfied as shown in FIGS. 17A and 17B in a narrow sense.

In addition, in the case of the disposition shown in FIG. 17B, the height h1 of the light-transmissive member 50 at a position or in a region corresponding to the first light receiving portion 140 may be set to be higher than the height h2 of the light-transmissive member 50 at a position or in a region corresponding to the second light receiving portion 141. For example, the convex portion 52-1 and the convex portion 52-2 may be installed as shown in FIG. 17A.

In the disposition shown in FIGS. 17A and 17B (hereinafter, also denoted as counter disposition since a plurality of light receiving portions face to each other based on the light emitting portion 150), an optical path from the light emitting portion 150 to the first light receiving portion 140 and an optical path from the light emitting portion 150 to the second light receiving portion 141 do not overlap each other. For this reason, the convex portion 52-1 and the convex portion 52-2 hardly interrupt each other, and therefore, it is advantageous in that it is easy to provide a difference between the height of h1 and the height of h2.

Figure 15B:
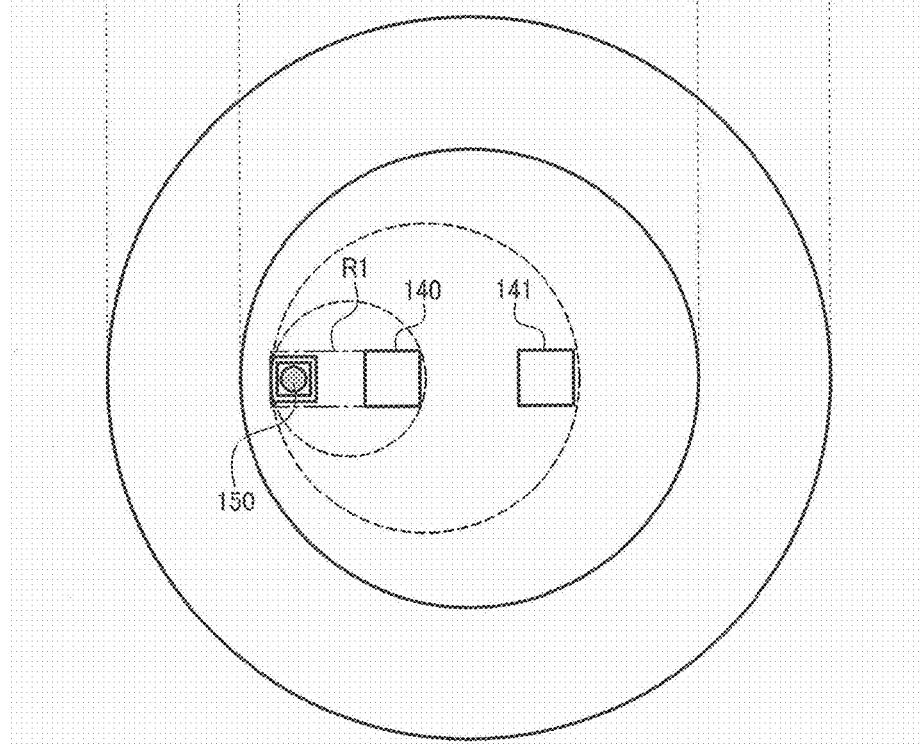
Figure 16B:
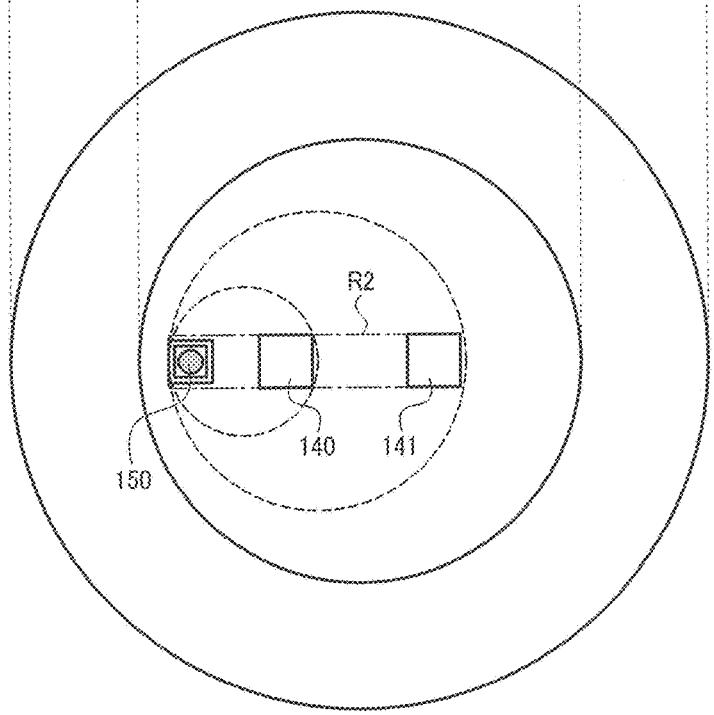
Figure 18A:
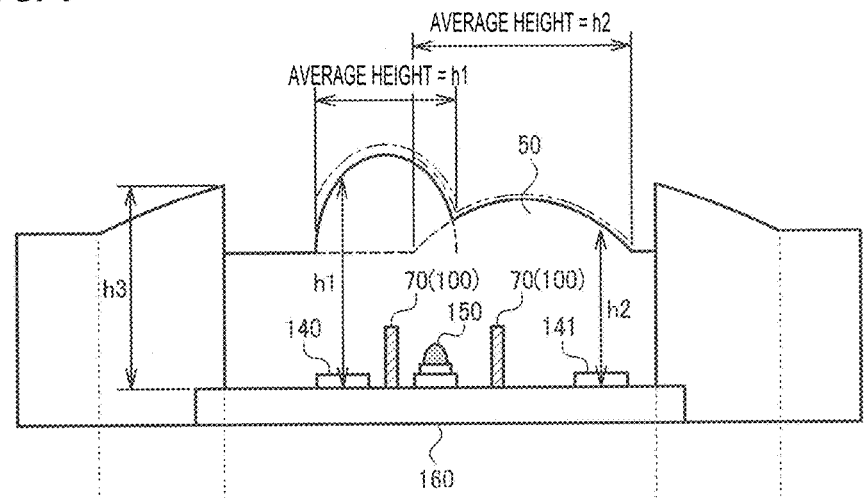
FIG. 18 shows views illustrating the height in the case of the opposed disposition.
Figure 18B:
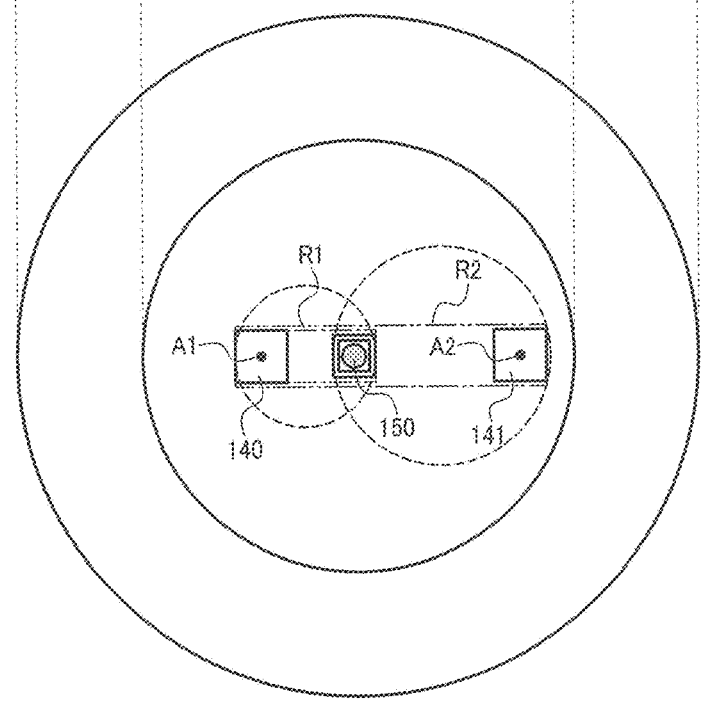

Specifically, as shown in FIG. 18B, the overlapping area between a region R1 corresponding to the first light receiving portion 140 and a region R2 corresponding to the second light receiving portion 141 becomes small compared to those shown in FIGS. 15B and 16B. For this reason, even when obtaining an average of heights, the overlapping area is small compared to the FIGS. 15A and 16A as shown in FIG. 18A, and therefore, it is easy to provide a difference in the heights.

Meanwhile, since the optical paths do not overlap each other, there is a concern that the degree of correlation between a first detection signal and a second detection signal may be decreased. As described above, it is preferable that each detection signal have a correlation to some extent while having different characteristics in order to increase the effect of the noise reduction processing. That is, if the correlation between the first and second detection signals is to be emphasized, it is considered that the configuration using the above-described disposition using FIG. 1A or the like is advantageous.

In addition, the light receiving portions share the light emitting portion 150 in both of FIGS. 1A and 17A, but a plurality of light emitting portions may be provided. For example, the biological information detecting device may include the light emitting portion 150 and the second light emitting portion 157 in order to realize a first photoelectric sensor using the light emitting portion 150 and the first light receiving portion 140 and to realize a second photoelectric sensor using the second light emitting portion 157 and the second light receiving portion 141.

Figure 19A:
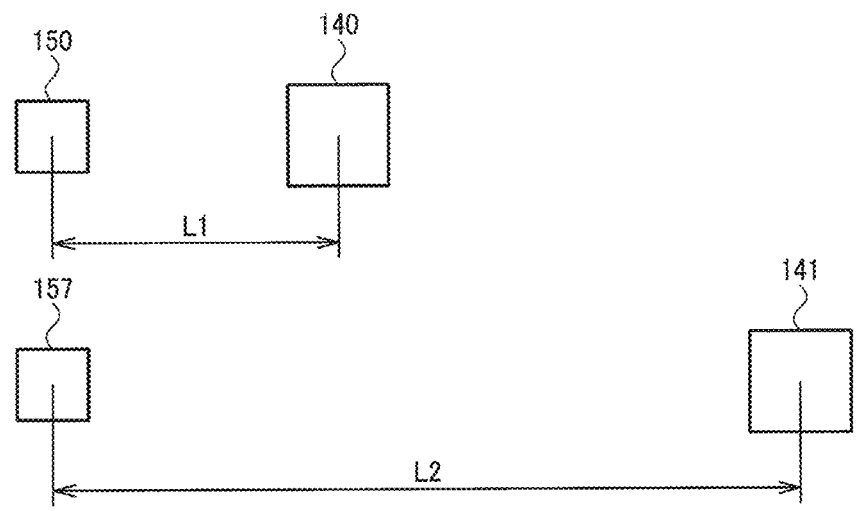
FIG. 19A is a disposition example in a case in which a plurality of light emitting portions are provided.
Figure 19B:
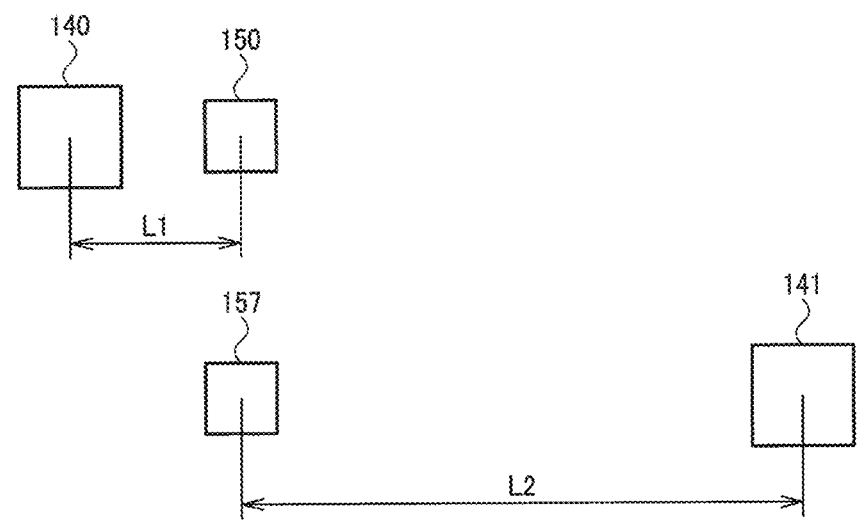
FIG. 19B is a disposition example in a case in which a plurality of light emitting portions are provided.

A disposition example of elements in this case on the substrate 160 is shown in FIGS. 19A and 19B. FIGS. 19A and 19B are examples in which light emitting portions and the like are observed in a plan view from a subject side, and the substrate 160 or the like is omitted in order to simplify the description. Similarly to FIG. 1A, FIG. 19A is an example in which a plurality of light receiving portions are provided on the same side with respect to the light emitting portion. In addition, FIG. 19A may have a counter disposition similarly to FIG. 17A, and the example of such a case is shown in FIG. 19B.

In addition, an example in which two photoelectric sensors are included in the biological information detecting device, that is, at least one light emitting portion and two light receiving portions are included is described above. However, the biological information detecting device is not limited thereto and the biological information detecting device may include three or more photoelectric sensors. In this case, all of the light receiving portions may share one light emitting portion, or light emitting portions forming a pair with each of the light receiving portions, or a combination thereof may also be employed. That is, the biological information detecting device may include first to N-th (where N is an integer of greater than or equal to 3) light receiving portions and a first to k-th (where k is an integer satisfying 1<=k<=N) light emitting portions.

3. Noise Reduction Processing

Finally, body motion noise reduction processing which is performed in the processing portion 200 will be described. Specifically, a spectrum subtraction method which is performed based on a second detection signal and adaptive filter processing which is performed based on a signal from a motion sensor will be described.

3.1 Spectrum Subtraction Method

Figure 20A:
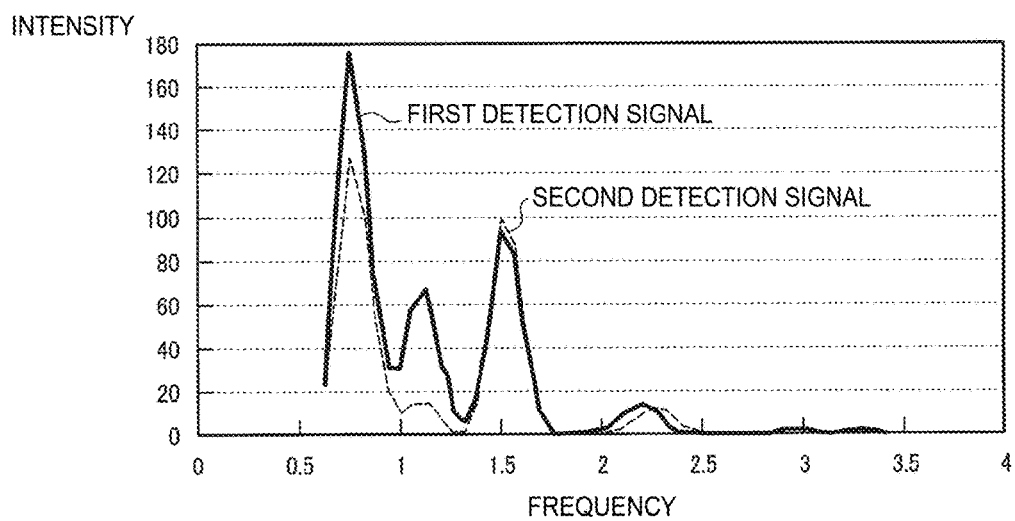
FIG. 20A is a view illustrating body motion noise reduction processing using a second detection signal.
Figure 20B:
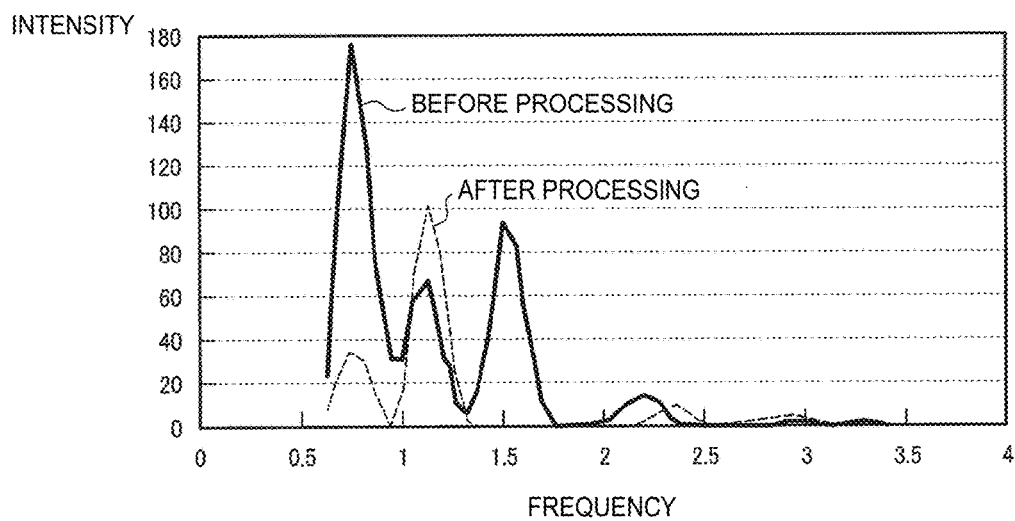
FIG. 20B is a view illustrating body motion noise reduction processing using a second detection signal.

FIGS. 20A and 20B are views illustrating noise reduction processing of a first detection signal based on a second detection signal. In the spectrum subtraction method, a spectrum is obtained by performing frequency conversion processing on each of the first and second detection signals. Then, processing of estimating a noise spectrum from a spectrum of the second detection signal and removing the estimated noise spectrum from a spectrum of the first detection signal is performed.

FIG. 20A shows the spectrum of the first detection signal and the spectrum of the second detection signal which are actually obtained. As described above, the spectrum of the second detection signal mainly becomes a spectrum corresponding to a noise component using the biological information detecting device according to the present embodiment. That is, it is possible to estimate that a frequency having a large peak in the spectrum of the second detection signal is a frequency corresponding to a body motion noise. In reality, only the peak in the spectrum of the second detection signal may be subtracted. However, the processing is not limited thereto, and for example, processing of subtracting the whole spectrum of the second detection signal from the whole spectrum of the first detection signal may be performed.

During the subtraction, any one of the first detection signal and the second detection signal is multiplied by a coefficient so as to cancel the noise, for example. The coefficient is obtained from the signal intensity of a predetermined frequency, for example. Alternately, the coefficient may be calculated such that the noise and the signal are separated from each other through a technique such as clustering and the intensity of the noise of the first detection signal and the intensity of the noise of the second detection signal are set to be the same as each other.

An example of the first detection signal before and after the body motion noise reduction processing using the spectrum subtraction method is shown in FIG. 20B. As can be seen from FIG. 20B, the body motion noises which appear at 0.7 Hz to 0.8 Hz (42 to 48 in a pulse rate) and 1.5 Hz (90 in a pulse rate) are suppressed so as to be small through the body motion noise reduction processing, and therefore, it is possible to suppress a possibility in which the body motion noises are erroneously determined as pulse signals. Meanwhile, it is possible to maintain the signal level with respect to the spectrum corresponding to pulse signals which appear below and above 1.1 Hz (66 in a pulse rate) without reducing the noises.

The spectrum subtraction method is realized through frequency conversion processing such as fast Fourier transform (FFT), and subtraction processing in the spectrum. Therefore, it is advantageous in that the algorithm is simple and the calculation quantity is small. In addition, there is no learning factor included such as adaptive filter processing which is to be described later, and therefore, the spectrum subtraction method has characteristics where instantaneous responsiveness is high.

3.2. Adaptive Filter Processing

Figure 21:
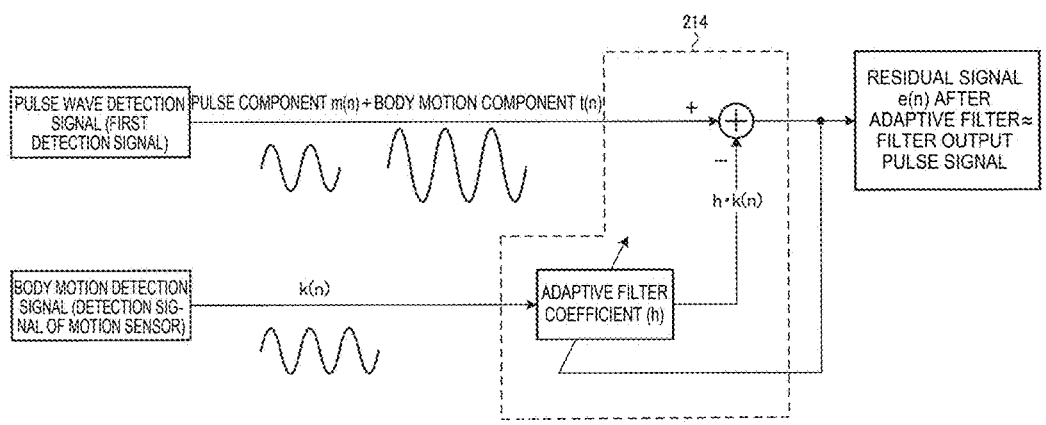
FIG. 21 is a view illustrating adaptive filter processing.

Next, body motion noise reduction processing (second body motion noise reduction processing) will be described based on a detection signal from a motion sensor through adaptive filter processing. A specific example of the noise reduction processing using an adaptive filter is shown in FIG. 21. Specifically, the detection signal of the motion sensor corresponds to a body motion noise, and therefore, in processing of removing a noise component specified from the detection signal from a first detection signal, the outline of the idea is the same as the spectrum subtraction method.

However, even if both the body motion noise in a pulse wave detection signal and a body motion detection signal from a body motion sensor are signals caused by the same body motion, their signal levels are not always the same as each other. Accordingly, an estimated body motion noise component is calculated by performing filter processing through which a filter coefficient is adaptively determined with respect to the body motion detection signal, and the difference between the pulse wave detection signal and the estimated body motion noise component is taken. It is possible to improve the accuracy of the noise reduction processing since the filter coefficient is adaptively determined (by performing learning). However, it is necessary to consider a processing load in determining the filter coefficient, or delay of an output. The adaptive filter processing is a well-known technique, and therefore, the detailed description thereof will be omitted.

In the present embodiment, the biological information detecting device has a motion sensor (acceleration sensor 172) as shown in FIG. 6, and the processing portion 200 performs second body motion noise reduction processing through which the body motion noise of the first detection signal is reduced based on a detection signal from the motion sensor.

That is, in the present embodiment, it is assumed that body motion noise reduction processing using a second detection signal from the second light receiving portion 141 is performed, but body motion noise reduction processing using the motion sensor may be used together. Accordingly, it is possible to more precisely reduce the body motion noise compared to the case in which only the body motion noise reduction processing using the second detection signal is performed. For example, noises at 0.7 Hz to 0.8 Hz, or 2.3 Hz to 2.4 Hz are not fully reduced as shown in FIG. 20B. However, it is possible to reduce the noises using processing, in which a detection signal from the motion sensor is used, together.

In addition, the processing portion 200 may perform the body motion noise reduction processing with respect to the first detection signal based on the second detection signal and perform the second body motion noise reduction processing with respect to the signal after the body motion noise reduction processing based on the detection signal from the motion sensor.

Figure 22:
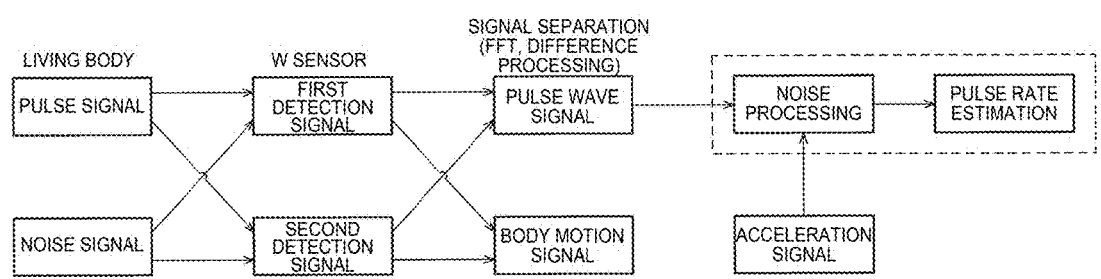
FIG. 22 is a view illustrating the flow of signal processing.

Accordingly, it is possible to perform a plurality of times of body motion noise reduction processing in a predetermined order. Here, as also shown in the functional block diagram of FIG. 6, first, the body motion noise reduction processing using the second detection signal is performed, and then, the second body motion noise reduction processing is performed. FIG. 22 shows the flow of each signal in this case.

It is possible to detect a pulse signal and a noise signal from a living body as shown in FIG. 22, and both of the signals are included in each detection signal from a plurality of light receiving portions. However, in the present embodiment, the ratio therebetween differs in each of the light receiving portions. The first detection signal has a relatively large number of pulse signals, and the ratio of the pulse signal in the second detection signal is low compared to the first detection signal (the ratio of the body motion noise is high). The pulse signals and the body motion signals (body motion noises) are separated from each other using the two detection signals. The processing is realized through the above-described spectrum subtraction method. The second body motion noise reduction processing using the detection signal (acceleration signal in FIG. 22) of the motion sensor is performed with respect to the separated pulse signals (first detection signal after the body motion noise reduction processing), and the pulse rate or the like is estimated from the result.

The present embodiment has been described in detail as described above. Those skilled in the art could easily understand that various modifications can be made within a range not departing from a new matter and effect of the invention. Accordingly, such modification examples are all considered to be included in the scope of the invention. For example, a term which is at least once described together with a different term having the same or broader meaning can be replaced with the different term. In addition, the configuration and the operation of the biological information detecting device or the like are also not limited to the present embodiment, and various modifications can be made.

The invention claimed is:

1. A biological information detecting device configured to detect a pulse wave of a subject, the device comprising:
   a substrate;
   at least one light source disposed on the substrate and which emits light to a subject;
   a first light receiving sensor disposed on the substrate and which receives light from the subject;
   a second light receiving sensor disposed on the substrate and which receives light from the subject;
   a light shielding wall disposed on the substrate between the light source and at least one of the first light receiving sensor and the second light receiving sensor; and
   a light-transmissive layer, which is provided over the substrate to cover the first light receiving sensor and the second light receiving sensor and at a position nearer to the subject than the first light receiving sensor and the second light receiving sensor, through which light from the subject is transmitted,
   wherein
      the light-transmissive layer is shaped to have a first height at a position or in a region corresponding to the first light receiving sensor and a second height at a position or in a region corresponding to the second light receiving sensor, the first height and the second height being measured in a direction from the substrate to the subject, and
      the first height is greater than the second height.

2. The biological information detecting device according to claim 1, wherein
   the first height is a height of the light-transmissive layer at a representative position of the first light receiving sensor, and the second height is a height of the light-transmissive layer at a representative position of the second light receiving sensor.

3. An electronic apparatus comprising the biological information detecting device according to claim 2.

4. The biological information detecting device according to claim 1,
wherein when a region including the first light receiving sensor and the light source in a plan view that is viewed from the subject side is a first region and a region including the second light receiving sensor and the light source in a plan view that is viewed from the subject side is a second region, the first height is an average height of the light-transmissive layer in the first region and the second height is an average height of the light-transmissive layer in the second region.

5. An electronic apparatus comprising the biological information detecting device according to claim 4.

6. The biological information detecting device according to claim 1, wherein
the light-transmissive layer is pressed against the subject at a time of measuring the biological information of the subject, and
when a pressing force of the light-transmissive layer at a position or in a region corresponding to the first light receiving sensor is P1 and a pressing force of the light-transmissive layer at a position or in a region corresponding to the second light receiving sensor is P2, P1>P2 is satisfied due to difference between the first height and the second height of the light-transmissive layer.

7. An electronic apparatus comprising the biological information detecting device according to claim 6.

8. The biological information detecting device according to claim 1, further comprising:
at least one processor that calculates the biological information of the subject based on a first detection signal detected by the first light receiving sensor.

9. An electronic apparatus comprising the biological information detecting device according to claim 8.

10. The biological information detecting device according to claim 1, wherein the first light receiving sensor is disposed on the substrate between the light source and the second light receiving sensor.

11. The biological information detecting device according to claim 10, wherein when a distance between a center of the light source and a center of the first light receiving sensor is L1 and a distance between the center of the light source and a center of the second light receiving sensor is L2, L2>2×L1 is satisfied.

12. An electronic apparatus comprising the biological information detecting device according to claim 11.

13. An electronic apparatus comprising the biological information detecting device according to claim 10.

14. The biological information detecting device according to claim 1, wherein when a distance between a center of the light source and a center of the first light receiving sensor is L1 and a distance between the center light source and a center of the second light receiving sensor is L2, L2>L1 is satisfied.

15. The biological information detecting device according to claim 14, wherein
the distance L1 between the center of the light source and the center of the first light receiving sensor satisfies 1 mm≤L1≤3 mm, and
the distance L2 between the center of the light source and the center of the second light receiving sensor satisfies 2 mm≤L2.

16. An electronic apparatus comprising the biological information detecting device according to claim 14.

17. The biological information detecting device according to claim 1, further comprising: wherein the light source is disposed on the substrate between the first light receiving sensor and the second light receiving sensor.

18. The biological information detecting device according to claim 1, further comprising:
a contact portion which is provided around the light-transmissive layer and comes into contact with the subject at the time of measuring the biological information of the subject,
wherein a third height at a position or in a region corresponding to the contact portion is greater than the first height and is less than the second height.

19. The biological information detecting device according to claim 1, wherein the light-transmissive layer has a curved surface-like convex portion.

20. An electronic apparatus comprising the biological information detecting device according to claim 1.

\* \* \* \* \*